(12) United States Patent
Fukushima et al.

(10) Patent No.: US 7,531,643 B2
(45) Date of Patent: May 12, 2009

(54) MONOCLONAL ANTIBODY INDUCING APOPTOSIS

(75) Inventors: Naoshi Fukushima, Gotemba (JP); Shinsuke Uno, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 249 days.

(21) Appl. No.: 10/355,236

(22) Filed: Jan. 31, 2003

(65) Prior Publication Data

US 2003/0211108 A1 Nov. 13, 2003

Related U.S. Application Data

(63) Continuation-in-part of application No. 09/508,251, filed as application No. PCT/JP98/04118 on Sep. 11, 1998, now abandoned.

(30) Foreign Application Priority Data

Sep. 11, 1997 (JP) ................... 9/264853

(51) Int. Cl.
C07K 16/00 (2006.01)
A61K 39/395 (2006.01)
(52) U.S. Cl. .............. 530/388.8; 530/387.1; 530/388.2; 530/388.85; 435/325; 435/326; 435/330; 435/344
(58) Field of Classification Search ........................ None
See application file for complete search history.

(56) References Cited

U.S. PATENT DOCUMENTS

| | | | |
|---|---|---|---|
| 5,837,242 A | 11/1998 | Holliger et al. | |
| 5,840,344 A | 11/1998 | Fukushima | |
| 5,885,574 A | 3/1999 | Elliott | |
| 6,342,220 B1 | 1/2002 | Adams et al. | |
| 6,579,692 B1 | 6/2003 | Fukushima | |
| 6,719,972 B1 | 4/2004 | Gribben et al. | |
| 6,759,043 B2 | 7/2004 | Fukushima | |
| 2003/0147894 A1 | 8/2003 | Fukushima et al. | |
| 2003/0157100 A1* | 8/2003 | Fukushima et al. | 424/143.1 |
| 2003/0157577 A1 | 8/2003 | Fukushima et al. | |
| 2003/0211108 A1 | 11/2003 | Fukushima et al. | |
| 2004/0058393 A1* | 3/2004 | Fukishima et al. | 435/7.2 |
| 2004/0073013 A1 | 4/2004 | Fukushima et al. | |

FOREIGN PATENT DOCUMENTS

| | | |
|---|---|---|
| EP | 0 721 015 A1 | 7/1996 |
| EP | 0 903 149 A1 | 3/1999 |
| EP | 1 035 132 | 9/2000 |
| EP | 1 262 548 B1 | 10/2008 |
| JP | 9 767 499 | 3/1997 |
| JP | 11-092500 | 4/1999 |
| WO | WO 91/16928 | 11/1991 |
| WO | WO 96/36360 A | 11/1996 |
| WO | WO 9732601 | 9/1997 |
| WO | WO 98/44001 A1 | 10/1998 |
| WO | WO 99/03495 A | 1/1999 |
| WO | WO 99/10494 | 3/1999 |
| WO | WO 99/12973 * | 3/1999 |
| WO | WO 99/17364 | 4/1999 |
| WO | WO 00/53634 A1 | 9/2000 |
| WO | 01/79494 * | 10/2001 |
| WO | WO 02/078612 A | 10/2002 |

OTHER PUBLICATIONS

Lindberg et al., 1993, Molecular Cloning of Integrin-associated Protein: An Immunoglobulin Family Member with Multiple Membrane-spanning Domains Implicated in Alpha(v)Beta(3)-dependent Ligand Binding, The J. of Cell Biology 123(2):485-496.*
Petterson, 2000, CD47 and death signalling in the immune system, Apoptosis 5:299-306.*
Dillman et al. (1989, Annals of Internal Medicine 111:592-603).*
Burthem et al., "Hairy Cell Interactions with Extracellular Matrix: Expression of Specific Integrin Receptors and Their Role in the Cell's Response to Specific Adhesive Proteins," Blood, vol. 84, No. 3, pp. 873-882. (1994).
Lindberg et al., "Rh-Related Antigen CD47 is the Signal-Transducer Integrin-Associated Protein," Communication, The Journal of Biological Chemistry, vol. 269, No. 3, pp. 1567-1570, (1994).
Mateo et al., "CD47 Ligation Induces Caspase-Independent Cell Death in Chronic Lymphocytic Leukemia," Articles, Nature America Inc., Nature Medicine, vol. 5, No. 11, pp. 1277-1284, (1999).
Schickel et al., "Gene for Integrin-Associated Protein (IAP, CD47): Physical Mapping, Genomic Structure, and Expression Studies in Skeletal Muscle," Biochem. Cell Biol., vol. 80, pp. 169-176, (2002).
Skolnick et al., "From Genes to Protein Structure and Function: Novel Applications of Computational Approaches in the Genomic Era," Review, Trends of Biotechnology, vol. 18, pp. 34-39, (2000).
Mateo et al., "Induction of Apoptosis in B-Cells From Chronic Lymphocytic Leukemia (B-CLLs) by CD47," FASEB Journal, vol. 12, No. 5, Mar. 20, 1998, p. A1082.
Fukushima et al., "Apoptosis of Bone Marrow Cells Via Integrin Associated Protein by the Novel Monoclonal Antibody," Blood, vol. 94, No. 10, Nov. 15, 1999, p. 479A.
N. Fukushima et al., Blood, vol. 80, No. 8, Enhanced Hematopoiesis In Vivo and In Vitro by Splenic Stromal Cells Derived From the Mouse With Recombinant Granulocyte Colony-Stimulating Factor, pp. 1914-1922 (1992).

(Continued)

Primary Examiner—Sheela J Huff
(74) Attorney, Agent, or Firm—Foley & Lardner LLP

(57) ABSTRACT

The monoclonal antibodies of this invention are antibodies that specifically recognize human Integrin Associated Protein, and the antigens that induce apoptosis of nucleated blood cells having human Integrin Associated Protein. Accordingly, they are useful as antibodies that recognize human Integrin Associated Protein for its distinction and identification, while also having an action of inducing apoptosis of nucleated blood cells; these properties can be utilized to prepare useful therapeutic agents in the field of treatment for myeloid leukemia and lymphoid leukemia.

3 Claims, 21 Drawing Sheets

OTHER PUBLICATIONS

F.P. Lindberg et al., The Journal of Cell Biology, vol. 123, No. 2, "Molecular Cloning of Integrin-associated Protein: An Immunoglobulin Family Member with Multiple Membrane-spanning Domains Implicated in αvβ3-dependent Ligand Binding," pp. 485-496 (1993).

M.I. Reinhold et al, Journal of Cell Science, vol. 108, "In vivo expression of alternatively spliced forms of integrin-associated protein (CD47)," pp. 3419-3425 (1995).

M.A. Schwartz et al., The Journal of Biological Chemistry, vol. 268, No. 27, "A 50-kDa Integrin-associated Protein Is Required for Integrin-regulated Calcium Entry in endothelial Cells," pp. 19931-19934 (1993).

D. Cooper et al., Proc. Nat;. Acad. Sci. USA, "Transendothelial migration of neutrophils involves integrin-associated protein (CD47)," pp. 3978-3982 (1995).

N. Itoh et al., Cell, vol. 66, The Polypeptide Encoded by the cDNA for Human Cell Surface Antigen Fas Can Mediate Apoptosis, pp. 233-243 (1991).

V. Bazil et al., "Apoptosis of Human hematopoietic Progenitor Cells Induced by Crosslinking of Surface CD43, the Major Sialoglycoprotein of Leukocytes," pp. 502-511 (1995).

L. Genestier et al., Blood, vol. 90, No. 2, "Antibodies to HLA Class I α 1 Domain Trigger Apoptosis of CD40-Activated Human B Lymphocytes," pp. 726-735 (1997).

J.F. Kearney et al., The Journal of Immunology, vol. 123, No. 4, "A New Mouse Myeloma Cell Line That Has Lost Immunoglobulin Expression But Permits The Construction of Antibody-Secreting Hybrid Cells Lines," pp. 1548-1550, (1979).

D.E. Yelton et al., "Fusion of Mouse Myeloma and Spleen Cells," Current Topics in Microbiology and Immunology, vol. 81, pp. 1-7 (1978).

G. Kohler et al., Eur. J. Immunol., vol. 6, "Derivation of specific antibody-producing tissue culture and tumor lines by cell fusion," pp. 511-519 (1976).

D.H. Margulies et al., Cell, vol. 8, "Somatic Cell Hybridization of Mouse Myeloma Cells," pp. 405-415 (1976).

M. Shulman et al., Nature, vol. 276, "A better cell line for making hybridomas secreting specific antibodies," pp. 269-270 (1978).

S. F. de St. Groth et al., Journal of Immunological Methods, vol. 35, "Production of Monoclonal Antibodies: Strategy and Tactics," pp. 1-21 (1980).

I.S. Trowbridge, J. Exp. Med., vol. 148, "Interspecies Spleen-Myeloma Hybrid Producing Monoclonal Antibodies Against Mouse Lymphocyte Surface Glycoprotein, T200," pp. 313-323 (1978).

G. Galfre et al., Nature, vol. 277, "Rat x rat hybrid myelomas and a monoclonal anti-Fd portion of mouse IgG," pp. 131-133 (1979).

G. Galfre et al., Methods in Enzymology, vol. 73, "Preparation of Monoclonal Antibodies: Strategies and Procedures," pp. 3-46 (1981.

L.W. Law et al., J. Natl. Cancer Inst., "Observations on the effect of a folic-acid antagonist on transplantable lymphoid leukemias in mice," pp. 179-192 (1949).

S. Mizushima et al., Nucleic Acids Research, vol. 18, No. 17, "pEF-BOS, a powerful mammalian expression vector," pp. 5322 (1990).

M. Shigeta et al., Clin Exp. Immunol., vol. 42, "Sperm-immobilizing monoclonal antibody to human seminal plasma antigens," pp. 458-462 (1980).

W. J. Mawby et al., Biochem. J., vol. 304, "Isolation and characterization of CD47 glycoprotein: a multispanning membrane protein which is the same as integrin-associated protein (IAP) and the ovarian tumour marker OA3," pp. 525-530 (1994).

Bartley, T., et al., "Identification and Cloning of a Megakaryocyte Growth and Development Factor That is a Ligand for the Cytokine Receptor Mpl," Cell, vol. 77, pp. 1117-1124 (1994).

Bazzoni et al., "Chimeric tumor necrosis factor receprors with constitutive signaling activity, " Proc. Natl. Acad. Sci. USA (Jun. 6, 1995), vol. 92, No. 12, pp. 5376-5580.

Berger, S. L., et al., "Inhibition of Intractable Nucleases with Ribonucleoside-Vanadyl Complexes: Isolation of Messenger Ribonucleic Acid From Resting Lymphocytes", Biochemistry, vol. 18, No. 23, pp. 5143-5149 (1979).

Caldas, C., et al., Mol. Immunol., vol. 39, No. 15, pp. 941-952 (2003).

Chien, N. C., et al., Proc. Natl. Acad. Sci. USA, vol. 84, No. 14, pp. 5532-5536 (1989).

Chirgwin, J. M., et al., "Isolation of Biologically Active Ribonucleic Acid from Sources Enriched in Ribonuclease", Biochemistry, vol. 18, No. 24, pp. 5294-5299 (1979).

de Sauvage, F., et al., "Stimulation of Megakaryocytopoiesis and Thrombopoiesis by the c-Mpl Ligand," Nature, vol. 369, pp. 533-538 (1994).

Deng, B., et al., "An Agonist Murine Monoclonal Antibody to the Human c-Mpl Receptor Stimulates Megakaryocytopoiesis," Blood, vol. 92, No. 6, pp. 1981-1988 (1991).

Felgenhauer, M., et al., "Nucleotide Sequences of the cDNAs Encoding the V-Regions of H- and L- Chains of a Human Monoclonal Antibody Specific to HIV-1—gp41," Nucleic Acids Research, vol. 18, No. 16, p. 4927 (1990).

Fujimoto, T., et al., Blood, vol. 86, No. 6, pp. 2174-2182 (1995).

Giusti, A. M., et al., Proc. Natl. Acad. Sci. USA, vol. 84, No. 9, pp. 2926-2930 (1987).

Goding, Monoclonal Antibodies: Principles and Practice, Academic Press, second Ed, pp.125-129 (1986).

Grell, M., et al., "TR50 and TR80 Tumor Necrosis Factor (TNF)-Receptors Can Independently Mediate Cytolysis", Lymphokine and Cytokine Research, vol. 12, No. 3, pp. 143-148 (Jun. 1993).

Gussow, D., et al., Methods in Enzymology, vol. 203, pp. 99-121 (1991).

Hopp, T., et al., "A Short Polypeptide Marker Sequence Useful for Recombinant Protein Identification and Purification," Bio/Technology, vol. 6, pp. 1204-1210 (1988).

Hudson, P. J., et al., "High avidity scFv multimers; diabodies and triabodies" J. Immunol. Methods, Elsevier Science Publishers, vol. 231, No. 1-2, pp. 177-189 (1999).

Huston, J., et al., "Protein Engineering of Antibody Binding Sites: Recovery of Specific Activity in an Anti-Digoxin Single-Chain Fv Analogue Produced in Escherichia coli," Proc. Natl. Acad. Sci. USA, vol. 85, pp. 5879-5883 (1988).

Kipriyanov, S., et al., "Bispecific CD3×CD19 Diabody for T Cell-Mediated Lysis of Malignant Human B Cells," Int. J. Cancer, vol. 77, pp. 763-772 (1988).

Larrick, J. W., et al., "Polymerase Chain Reaction Using Mixed Primers: Cloning of Human Monoclonal Antibody Variable Region Genes From Single Hybridoma Cells", Bio/Technology, vol. 7, pp. 934-938 (1989.

Lei, S. et al., "Characterization of the Erwinia caratovora pelB Gene and Its Product Pectate Lyase," J. Bacteriol., pp. 4379-4383 (1987).

Mariuzza, R. A., et al., Annu. Rev. Biophys. Biophys. Chem., vol. 16, pp. 139-159 (1987).

Methia, N., et al., "Oligodeoxynucleotides Antisense to the Proto-Oncogene c-Mpl Specifially Inhibit In Vitro Megakaryocytopoiesis," Blood, vol. 82, No. 5, pp. 1395-1401 (1993).

Milili, M., et al., "The VDJ Repertoire Expressed in Human preB Cells Reflects the Selection of Bona Fide Heavy Chains," Eur. J. Immunol., vol. 26, pp. 63-69 (1996).

Nakayama, et al., J. Mole. Med., vol. 83, pp. 316-320 (2005).

O'Brien et al., "Monoclonal antibodies for the human insulin receptor stimulate intrinsic receptor-kinase activity," Biochim. Soc. Trans. (1986), vol. 14, No. 6, pp. 1021-1023.

Paul, Fundamental Immunology, Raven Press, NY, Chapter 8, p. 242 (1993).

Riechmann, L., et al., "Reshaping Human Antibodies for Therapy", Nature, vol. 332, pp. 323-327 (1988).

Roue, G., et al., Biochimie, vol. 85, pp. 741-746 (2003).

Rozsnyay et al., "Phenylarsine oxide (PAO) blocks antigen receptor-induced calcium response and tyrosine phosphroylation of a distinct group of proteins," Immunology Lett. (Aug. 1993.), vol. 37, Nos. 2-3, pp. 197-205.

Rudikoff, et al., Proc. Natl. Acad. Sci. USA vol. 79, p. 1979 (1982).

Souyri, M., et al., "A Putative Truncated Cytokine Receptor Gene Transduced by the Myeloproliferative Leukemia Virus Immortalizes Hematopoietic Progenitors, " Cell, vol. 63, Dec. 21, pp. 1137-1147 (1990).

Spaargaren, M., et al., "Antibody-induced Dimerization Activates the Epidermal Growth Factor Receptor Tyrosine Kinase", The J. Biol. Chem., vol. 266, No. 3, pp. 1733-1739 (1981).

Xie, et al., "Direct demonstration of MuSK involvement in acetylcholine receptor clustering through identification of agonist ScFv," Nature Biotechnology, vol. 15, pp. 768-771 (1997).

Yanabu et al., "Tyrosine phosphorylation and p72syk activation by an anti-glycoprotein lb monoclonal antibody," *Blood* (1997), vol. 89, No. 5, pp. 1590-1598.

Yarden et al., "Self-phosphorylation of epidermal growth factor receptor: evidence for a model of intermolecular allosteric activisation," *Biochemistry* (1987), vol. 26, No. 5, pp. 1434-1442.

Greenspan et al., "Defining epitopes: It's not as easy as it seems," Nature Biotechnology, vol. 17, Oct. 1999, pp. 936-937.

Avent et al., "Monoclonal antibodies that recognize different membrane proteins that are deficient in $Rh_{null}$ human erythrocytes," Biochem. J., 1988, vol. 251, pp. 499-505.

Brown et al., "Integrin-associated Protein: A 50-kD Plasma Membrane Antigen Physically and Functionally Associated with Integrins," J. Cell Biology, Dec. 1990, vol. 111, No. 6, pt. 1, pp. 2785-2794.

Desplancq et al., "Multimerization behaviour of single chain Fv variants for the tumour-binding antibody B72.3," Protein Eng., Aug. 1994, vol. 7, No. 8, pp. 1027-1033 (Abstract).

Dorai et al., "Mammalian cell expression of single-chain Fv (sFv) antibody proteins and their C-terminal fusions with interleukin-2 and other effector domains," Biotechnology, Sep. 1994, vol. 12, No. 9, pp. 890-897 (Abstract).

Jiang et al., "A Novel Peptide Isolated from a Phage Display Peptide Library with Trastuzumab Can Mimic Antigen Epitope of HER-2," J. Biol. Chem., Feb. 11, 2005, vol. 280, No. 6, pp. 4656-4662.

Keen et al., "The use of serum-free medium for the production of functionally active humanized monoclonal antibody from NS0 mouse myeloma cells engineered using glutamine synthetase as a selectable marker," Cytotechnology, Jan. 1994, vol. 18, No. 3, pp. 207-217 (Abstract).

Kortt et al., "Recombinant anti-sialidase single-chain variable fragment antibody: Characterization, formation of dimmer and higher-molecular-mass multimers and the solution of the crystal structure of the single-chain variable fragment/sialidase complex," Eur. J. Biochem., 1994, vol. 221, pp. 151-157.

Kortt et al., "Single-chain Fv fragments of anti-neuraminidase antibody NC10 containing five- and ten- residue linkers form dimmers and with zero-residue linker a trimer," Protein Engineering, 1997, vol. 10, No. 4, pp. 423-433.

Petterson et al., "CD47 Signals T Cell Death," J. Immunol., 1999, pp. 7031-7040.

Reinhold et al., "In vivo expression of alternatively spliced forms of integrin-associated protein (CD47)," J. Cell Science, 1995, vol. 108, pp. 3419-3425.

Reiter et al., "Engineering interchain disulfide bonds into conserved framework regions of Fv fragments: improved biochemical characteristics of recombinant immunotoxins containing disulfide-stabilized Fv," Protein Engineering, 1994, vol. 7, No. 5, pp. 697-704.

Reiter et al., "Stabilization of the Fv Fragments in Recombinant Immunotoxins by Disulfide Bonds Engineered into Conserved Framework Regions," Biochemistry, 1994, vol. 33, pp. 5451-5459.

Stancovski et al., "Mechanistic aspects of the opposing effects of monoclonal antibodies to the ERBB2 receptor on tumor growth," Proc. Natl. Acad. Sci. USA, Oct. 1991, vol. 88, pp. 8691-8695.

Verma et al., "Antibody engineering: Comparison of bacterial, yeast, insect and mammalian expression systems," Journal of Immunological Methods, 1998, vol. 216, pp. 165-181.

Brown et al., "Integrin-associated protein (CD47) and its ligands," Trends in Cell Biology, Mar. 2001, 11(3), 130-135.

Deng et al., "An Agonist Murine Monoclonal Antibody to the Human c-Mpl Receptor Stimulates Magakaryocytopoiesis," Blood, Sep. 15, 1998, 92(6), 1981-1988.

Horan et al., "Dimerization of the Extracellular Domain of Granulocyte-Colony Stimulating Factor Receptor by Ligand Binding: A Monovalent Ligand Induces 2:2 Complexes," Biochemistry, 1996, 35, 4886-4896.

Schmidt et al., "A bivalent single-chain antibody-toxin specific for ErbB-2 and the EFG receptor," Int. J. Cancer, 1996, 65(4):538-546.

* cited by examiner

MONOCLONAL ANTIBODY INDUCING APOPTOSIS

This application is a continuation-in-part of U.S. patent application Ser. No. 09/508,251, filed on Apr. 10, 2000 and now abandoned, which is a national phase application of International Application Serial No. PCT/JP98/04118, filed on Sep. 11, 1998,which claims priority to Japanese Patent Application Serial No. 9/264853, filed on Sep. 11, 1997. All disclosures are hereby incorporated by reference in their entirety and relied upon.

TECHNICAL FIELD

This invention relates to novel monoclonal antibodies having the property of inducing apoptosis of nucleated blood cells with Integrin Associated Protein (IAP) as well as fragments of such monclonal antibodies, peptides or low molecular weight compounds, and to hybridoma that produce the monoclonal antibodies. The novel antibodies are useful as therapeutic agents for myeloid leukemia and lymphoid leukemia.

BACKGROUND ART

Granulocyte colony-stimulating factors, such as recombinant granulocyte colony-stimulating factor (rG-CSF), have been known in the prior art as humoral factors that stimulate differentiation and proliferation of granulocytes. Reports based on in vivo experiments with mice have shown that administration of rG-CSF results in not only accelerated myelopoiesis in bone marrow but also notable extramedullary hemopoiesis in the spleen, and proliferation of all hemopoietic precursor cells, including hemopoietic stem cells, in the spleen. The mechanism of such extramedullary hemopoiesis in the spleen has been believed that stimulation by rG-CSF alters the hemopoietic microenvironment of the spleen and promotes the hemopoiesis supporting ability thereof, thus inducing hemopoiesis.

In order to elucidate the hemopoietic function in the spleen, the present inventors have previously focused on stromal cells of the spleen following repeated administration of rG-CSF. The inventors have made efforts to examine how the hemopoietic function is promoted by rG-CSF via stromal cells, and have established a hemopoietic stromal cell line (CF-1 cells) from mouse spleen by repeated administration of rG-CSF. The inventors have studied the hemopoiesis-supporting ability of the hemopoietic stromal cells and confirmed the colony-stimulating activity in vitro and the hemopoietic stem cell-supporting ability in vivo [Blood, 80, 1914 (1992)].

However, while one cell line of the splenic stromal cells has been established (CF-1 cells) and its cytological characteristics have been studied, specific antibodies that recognize the surface antigens of these cells have never been prepared, nor have their characteristics been elucidated yet in any way.

DISCLOSURE OF INVENTION

In light of the aforementioned findings relating to splenic stromal cells and the results of prior research, the present inventors have earnestly made further research aiming at developing specific antibodies that can recognize the splenic stromal cells, made efforts to prepare monoclonal antibodies using the aforementioned splenic stromal cell line as a sensitizing antigen, and finally succeeded in obtaining novel monoclonal antibodies.

The inventors have further studied the properties of the monoclonal antibodies obtained as above and found that the monoclonal antibodies have the property of inducing myeloid cell apoptosis. These monoclonal antibodies have been designated "BMAP-1 antibody", which will be hereinafter referred to as such.

The inventors have also examined the antigen recognized by BMAP-1 antibody and found that it is mouse Integrin Associated Protein (mouse IAP) (GenBank, Accession Number Z25524) by direct expression cloning.

The action of BMAP-1 antibodies has been studied using recombinant cells into which the gene for mouse IAP had been introduced. Specifically, the mouse IAP gene was introduced into mouse Jurkat cells, which did not express mouse IAP, by a conventional method to create a mouse IAP-expressing cell line (recombinant Jurkat cells), and the action of BMAP-1 antibody on the mouse IAP-expressing cells has been investigated by MTS assay and DNA fragmentation by using flow cytometry (Japanese Patent Application No. HEI 9-67499).

It has been expected upon these findings that monoclonal antibodies for the antigen of human Integrin Associated Protein (hereinafter referred to as human IAP; amino acid sequence and base sequence described in J. Cell Biol., 123, 485-496, 1993; see also Journal of Cell Science, 108, 3419-3425, 1995) should have an effect of inducing apoptosis of nucleated blood cells that express this antigen (myeloid cells and lymphocytes), and the present inventors have made efforts to prepare monoclonal antibodies for the antigen of human Integrin Associated Protein and succeeded in obtaining monoclonal antibodies that induce apoptosis of human nucleated blood cells expressing this antigen.

In other words, itis an object of this invention to provide novel monoclonal antibodies having the property of inducing apoptosis of nucleated blood cells (myeloid cells and lymphocytes) with human Integrin Associated Protein (human IAP), and fragments thereof, as well as hybridomas that produce the monoclonal antibodies.

These novel monoclonal antibodies are useful as therapeutic agents for myeloid leukemia and lymphoid leukemia.

The reported functions of Integrin Associated Protein are the action of binding with the β chain of integrin αVβ3 to support binding between αVβ3 and its ligand vitronectin (J. Cell. Biol., 123, 485-496 (1993)), that of inducing inflow of $Ca^{2+}$ into the vascular endothelium upon adhesion of neutrophils with the vascular endothelium (J. Biol. Chem., 268, 19931-19934 (1993)), and that of supporting migration of neutrophils through the vascular endothelium (Proc. Natl. Acad. Sci. USA, 92, 3978-3982 (1995)), but no reports have been published on its function relating to apoptosis of nucleated blood cells.

The monoclonal antibodies of the invention are antibodies that specifically recognize human Integrin Associated Protein. They therefore exhibit a function of distinguishing and identifying human Integrin Associated Protein.

In addition, the monoclonal antibodies of the invention are antibodies that exhibit the property of inducing apoptosis of nucleated blood cells (myeloid cells and lymphocytes) with human Integrin Associated Protein. Apoptosis is a phenomenon in which nuclear chromatin DNA is cleaved into nucleosome units (known as a "ladder formation"), resulting in death of the cell and which is also referred to as cell suicide.

Monoclonal antibodies hitherto known to have the property of inducing apoptosis of nucleated blood cells (myeloid cells and lymphocytes) include anti-Fas antibody (Cell, 66; 233-243, 1991), anti-CD43 antibody (Blood, 86, 502-511, 1995) and anti-HLA Class Iα1 Domain antibody (Blood, 90, 726-735, 1997). The monoclonal antibodies of the invention are defined as encompassing any monoclonal antibody capable of specifically recognizing Integrin Associated Protein and having the property of inducing apoptosis of nucleated blood cells (myeloid cells and lymphocytes) with Integrin Associated Protein, preferably other than IF7.

The antibodies of the invention are not limited only to those that induce apoptosis of all nucleated blood cells. They also include those that induce apoptosis of at least one type of nucleated blood cells. Specifically, it sufficient in the case of myeloid leukemia to induce apoptosis of at least myeloid cells.

More specifically, this invention provides monoclonal antibodies that induce apoptosis of nucleated blood cells having Integrin Associated Protein (IAP).

The invention further provides fragments of monoclonal antibodies, peptides or low molecular weight comopunds that induce apoptosis of nucleated blood cells having Integrin Associated Protein (IAP).

The invention still further provides hybridomas that produce the monoclonal antibodies.

The invention still further provides an antileukemic agent that contains a substance that binds to IAP and promotes the action of IAP to induce apoptosis of nucleated blood cells.

The invention still further provides an antileukemic agent characterized in that the substance is a monoclonal antibody.

The invention still further provides an antileukemic agent characterized in that the substance is a fragment of a monoclonal antibody, a peptide or a low molecular weight compound.

BEST MODE FOR CARRYING OUT THE INVENTION

Preparation of Monoclonal Antibody

Figure 1:
FIG. 1 is an electrophoresis pattern showing a band for human-IAP amplified by PCR using cDNA prepared from mRNA of HL-60 cell line. From left are shown a molecular weight marker (M), human IAP (1) and β-actin (2).

The monoclonal antibodies of this invention can generally be prepared in the following manner. That is, monoclonal antibodies of the invention may be obtained, for example, by using human Integrin Associated Protein as the sensitizing antigen, immunizing animals with the antigen by an immunization method known in the art, performing cell fusion by a cell fusion method known in the art and cloning by a cloning method known in the art.

More specifically, a preferable method of preparing monoclonal antibodies of the invention is, for example, a method wherein recombinant cells of the mouse leukemia cell line L1210 that express human Integrin Associated Protein are used as the sensitizing antigen, plasma cells (immunocytes) of a mammal immunized with the sensitizing antigen are fused with myeloma cells of mammals such as mice, the resulting fused cells (hybridomas) are cloned, the clones producing the antibodies of the invention that recognize the aforementioned cell line are selected from the resulting clones and cultured, and the target antibodies are obtained.

The above method is merely one possible example of the invention and, for example, the sensitizing antigen is not limited to the aforementioned L1210 recombinant cells but may also be human Integrin Associated Protein (IAP) itself, or human IAP in soluble form; the target monoclonal antibodies that induce apoptosis of nucleated blood cells (myeloid cells and lymphocytes) can be prepared in the same manner as in the L1210 recombinant cells mentioned above.

The phage display method may also be used to prepare a target monoclonal antibody from a cDNA library for the antibody.

The mammals to be immunized with the sensitizing antigen in the method of preparing the monoclonal antibodies are not particularly limited, but they are preferably selected in consideration of their compatibility with the myeloma cells used for cell fusion, and mice, rats, hamsters and the like are general suitable.

The immunization is preferably accomplished by a standard method. For example, the human Integrin Associated Protein-expressing L1210 recombinant cells are administered to the animal by intraperitoneal injection or the like. More specifically, an appropriate dilution or suspension with PBS or physiological saline is preferably administered to the animal a few times at 10-day intervals. The immunocytes used are preferably spleen cells extracted after the final administration of the cells.

The mammalian myeloma cells used as the parent cells for fusion with the immunocytes may be any of various cell lines known in the art, for example, P3 (P3×63Ag8.653) [J. Immunol., 123, 1548 (1978)], P3-U1 [Current Topics in Microbiology and Immunology, 81, 1-7 (1978)], NS-1 [Eur. J. Immunol., 6, 511-519 (1976)], MPC-11 [Cell, 8, 405-415 (1976)], Sp2/0-Ag14 [Nature, 276, 269-270 (1978)], FO [J. Immunol. Meth., 35, 1-21 (1980)], S194 [J. Exp. Med., 148, 313-323 (1978)] and R210 [Nature, 277, 131-133 (1979)].

The cell fusion between the immunocytes and myeloma cells may be performed basically according to a conventional method, such as the method of Milstein et al. [Methods Enzymol., 73, 3-46 (1981)].

More specifically, the cell fusion is carried out, for example, in a common nutrient medium in the presence of a fusion promoter. For example, the fusion promoter used may be polyethylene glycol (PEG), Sendai virus (HVJ) or the like, and, if desired, an adjuvant such as dimethyl sulfoxide may also be added appropriately in order to increase fusion efficiency. The immunocytes are used preferably in the amount of 1-10 times as much as myeloma cells. The medium used for the cell fusion may be, for example, RPMI-1640 medium, MEM medium and the like, which are suitable for growth of myeloma cell lines, or other media commonly used for such cell culturing, and it may also be used in combination with a serum supplement such as fetal bovine serum (FBS).

The cell fusion is carried out by thoroughly mixing prescribed amounts of the immunocytes and myeloma cells in the medium, adding a solution of PEG preheated to about 37° C., the PEG having an average molecular weight of approximately 1;000-6,000, for example, to the medium usually at a concentration of about 30-60% (W/V), and mixing. A suitable medium is then successively added, and the supernatant obtained by centrifugation is removed. This procedure is repeated to produce the target hybridomas.

The hybridomas are selected by culturing in a common selection medium, such as HAT medium (a medium, containing hypoxanthine, aminopterin and thymidine). Culturing in the HAT medium is continued for a sufficient time to allow death of all the cells other than the target hybridomas (all the non-fused cells), which is usually from a few days to a few weeks. The usual limiting dilution method is then employed for screening and monocloning of hybridomas producing the target antibodies.

The hybridomas prepared in this manner that produce the monoclonal antibodies of the invention may be subcultured in common medium, and may be placed in long-term storage in liquid nitrogen.

In order to obtain the monoclonal antibodies of the invention from the hybridomas, any suitable methods may be employed, such as a method wherein the hybridomas may be cultured according to standard methods and the antibodies may be obtained from the culture supernatants; or alternatively, a method wherein the hybridomas may be administered to a compatible mammal for proliferation and then the antibodies may be obtained from the ascites fluid thereof. The former method is suitable for obtaining highly, pure antibodies, while the latter method is more suited for mass production of antibodies.

The antibodies obtained by the aforementioned methods can be highly purified by utilizing standard, purification methods such as salting-out, gel filtration, affinity chromatography, or the like.

Monoclonal Antibody Fragments

The monoclonal antibodies of this invention may be the complete antibodies described above, or fragments thereof. That is, they may be any fragments of a monoclonal antibody of the invention that specifically recognize human Integrin Associated Protein and induce apoptosis of nucleated blood cells (myeloid cells and lymphocytes) having human Integrin Associated Protein. Such fragments include Fab, F(ab')$_2$, Fab', etc. These fragments can be prepared by digestion with an enzyme such as papain, pepsin, ficin or the like. The properties of the obtained fragments can be confirmed in the same manner as described above.

Peptides and Low Molecular Weight Compounds Having the Same Function as the Monoclonal Antibodies The monoclonal antibodies described above, which recognize human Integrin Associated Protein and induce apoptosis of nucleated blood cells, also encompass peptides and low molecular weight compounds that likewise recognize IAP and induce apoptosis of nucleated blood cells.

Properties of Monoclonal Antibodies of the Invention

As specifically described in the following Examples, the monoclonal antibodies of the invention specifically recognize human Integrin Associated Protein.

The monoclonal antibodies of the invention also induce apoptosis of nucleated blood cells (myeloid cells and lymphocytes) with human Integrin Associated Protein.

The monoclonal antibodies of the invention are not IF7.

These properties can be utilized to obtain useful therapeutic agents in the field of treatment for myeloid leukemia and lymphoid leukemia.

Thus, it will be readily appreciated that the construction of specific systems involving the use of the monoclonal antibodies of the invention, as antibodies to specifically recognize an antigen that causes apoptosis of nucleated blood cells, for distinction and identification of the antigens, or the use of the unique properties of the monoclonal antibodies as therapeutic agents for myeloid leukemia and lymphoid leukemia, as well as any modifications and applications of the system, are also within the scope of this invention insofar as they can be carried out by applying standard methods that are obvious to those skilled in the art.

Antileukemic Agents

An antileukemic agent according to this invention is based on the fact that the action of IAP is promoted by binding of an antibody or the like of the invention. While there are no particular limitations on the dose of the antibody of the invention, it is preferably in the range of 5 μg to 500 mg/kg.

EXAMPLES

This invention will now be explained in greater detail by way of the following examples; however, the invention is not to be limited to these examples.

Example 1

Monoclonal Antibody Preparation (1) Sensitizing Antigen and Immunization Method

Antigen sensitization was accomplished using a recombinant cell line as the sensitizing antigen, which was the L1210 cells transfected with human IAP gene and highly expressed the product. L1210 is obtained from the DBA mouse-derived leukemia cell line (ATCC No. CCL-219, J. Natl. Cancer Inst. 10:179-192, 1949).

The human IAP gene was amplified by PCR using a primer with a human IAP-specific sequence (sense primer: GCAAGCTTATGTGGCCCCTGGTAGCG (SEQ ID NO: 1), antisense primer: GCGGCCGCTCAGTTATTCCTAG-GAGG) (SEQ ID NO: 2) and cDNA prepared from mRNA of HL-60 cell line (Clontech laboratories, Inc.) as the template (FIG. 1)

The PCR product was subcloned into a cloning vector pGEM-T (Promega Corporation) and used to transform *E. coli* JM109 (Takara. Shuzo Co., Ltd.), and after confirming the nucleotide sequence of the insert DNA with a DNA sequencer (373A DNA Sequencer, available from ABI), it was subcloned with an expression vector pCOS1.

Expression vector pCOS1 is a derivative of pEF-BOS (Nucleic Acids Research, 18, 5322, 1990), and it is a vector obtained by subcloning the neomycin resistant gene using human elongation factor-1α as a promoter/enhancer. This human IAP-subcloned expression vector was used for gene introduction into L1210 cell line with DMRIE-C (GIBCO/BRL), selection was performed with Geneticin (final concentration: 1 mg/ml, available from GIBCO/BRL), and the gene-introduced L1210 cells were cloned by the limiting dilution method.

Figure 2:
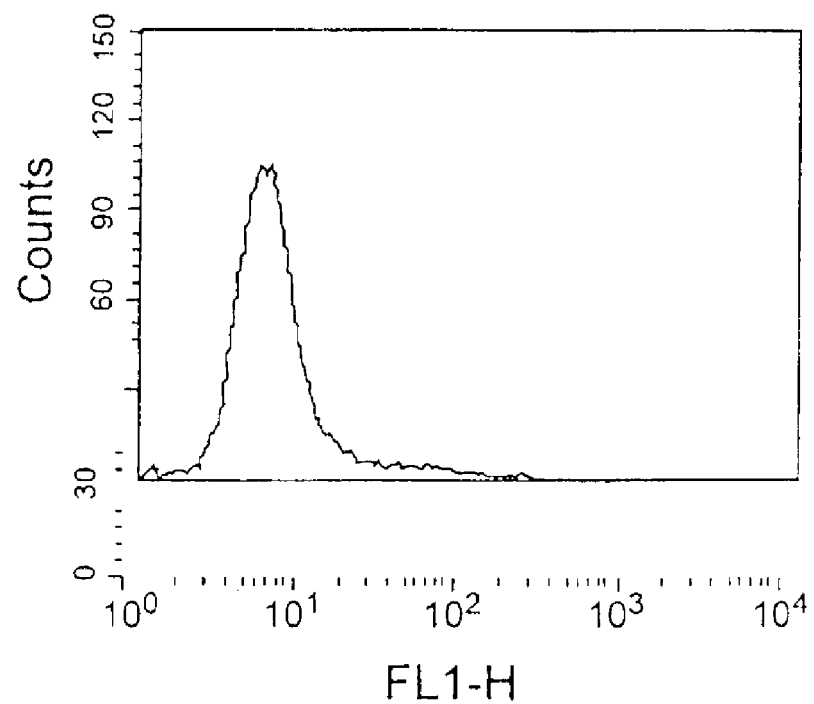
FIG. 2 is a graph showing the level of expression of human IAP by L1210 cells that have expressed human IAP, using anti-CD47 antibody. The peak represents L1210 cells transfected with only pCOS1 gene as a control.
Figure 3:
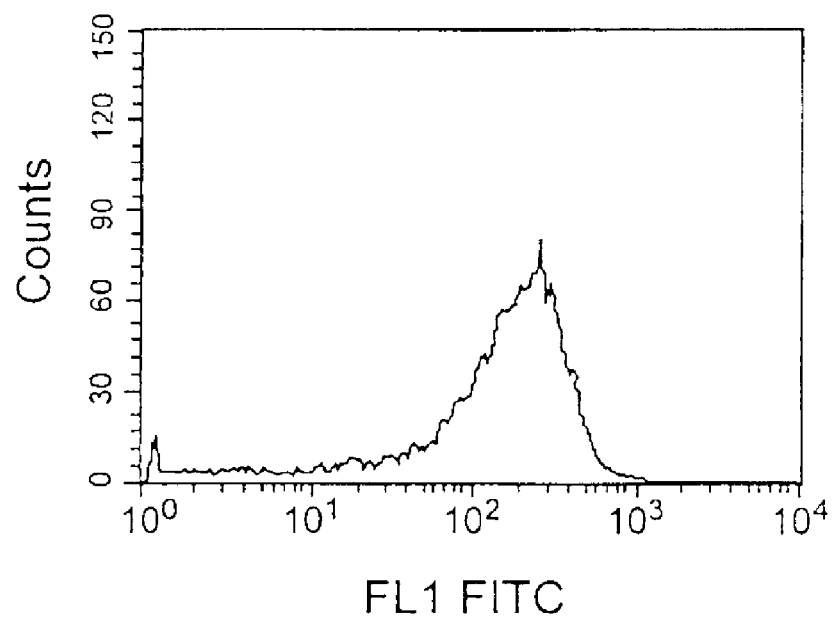
FIG. 3 is another graph showing the level of expression of human IAP by L1210 cells that have expressed human IAP, using anti-CD47 antibody. The peak shows that human IAP expression has definitely increased in L1210 cells transfected with the human IAP gene.

The antigen expression of the obtained clones was examined using human IAP-recognizing anti-CD47 antibody (PharMingen), and the clones with high levels of expression were selected as antigen-sensitized cells (FIGS. 2, 3). For culturing of the recombinant L1210 cells, 10% fetal bovine serum (FBS, available from Moregate Inc.) and Iscove's-Modified Dulbecco's Medium (IMDM) (GIBCO/BRL) were used as the medium and the cells were subcultured in a 5% $CO_2$ incubator at a temperature of 37° C.

The immunized animals used were DBA/2 mice (bred by Charles River, Japan), which were of the same strain as the L1210 cells. The human Integrin Associated Protein (IAP) gene-transfected L1210 cells, used for antigen, sensitization, were incubated for about 30 min with mitomycin C (Kyowa Hakko Kogyo Co., Ltd.) at a concentration of 200 μg/ml, and after suspending growth of the cells, mitomycin C was thoroughly washed off prior to suspension in PBS.

Figure 4:
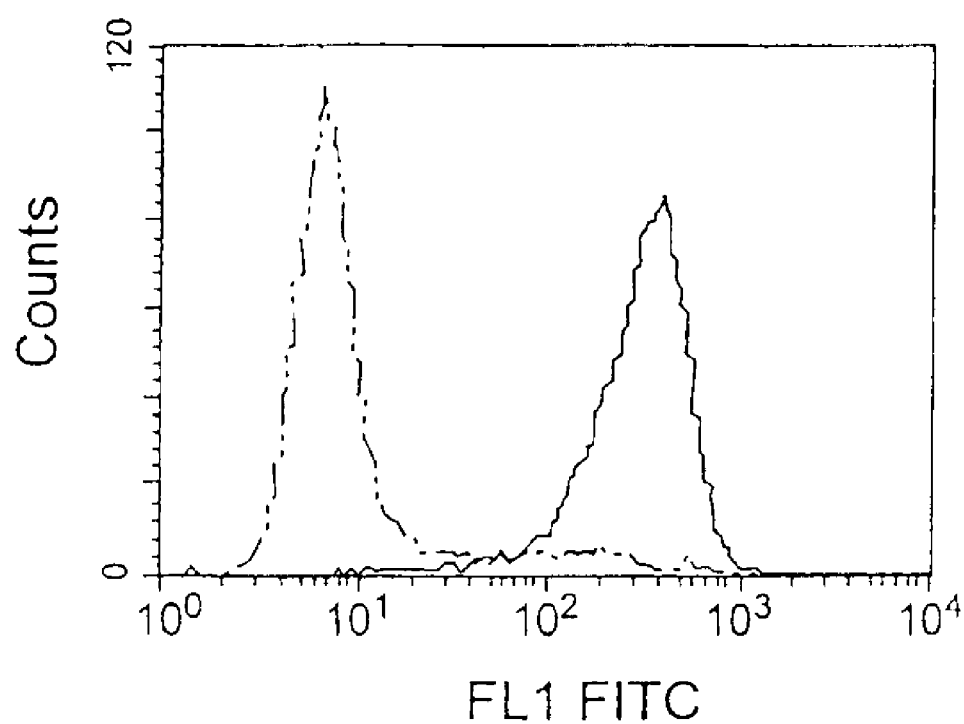
FIG. 4 is a graph showing antibody titers in immunized mice. The left peak represents intact L1210 cells. The right peak represents L1210 cells transfected with human IAP, showing that the serum of the mouse subjected to cell fusion clearly recognizes human IAP.

The cells were intraperitoneally injected into the mice three times at intervals of about 10 days, at approximately $5 \times 10^6$ cells each time. After the third immunization, blood was taken from the eye socket, the serum was diluted 50-fold with PBS containing 1% BSA, and binding between the diluted serum and the recombinant L1210 cells used for antigen sensitization was confirmed with a FACScan (Becton Dickinson and Company) (FIG. 4); the mouse having the best antiserum activity was subjected to a booster immunization with intraperitoneal injection of $1 \times 10^7$ cells 5 days after the fourth immunization. Four days after the final immunization, the mouse was sacrificed and the spleen extracted.

(2) Cell Fusion

After thinly slicing the spleen extracted from the mouse, the dissociated spleen cells were centrifuged and then suspended in IMDM medium, allowed to float, and thoroughly rinsed. Separately, the mouse myeloma cell line P3-U1 [Current Topics in Microbiology and Immunology, 81, 1-7 (1978)] was cultured in IMDM medium containing 10% fetal bovine serum (FBS, available from Moregate Inc.), and after rinsing similarly with the IMDM medium, the $1 \times 10^7$ cells were placed in a centrifuge tube in admixture with $5 \times 10^7$ cells of the spleen cells and subjected to cell fusion according to a standard method [Clin. Exp. Immunol. 42, 458-462 (1980)], using polyethylene glycol 4000 (Nakaral Chemical Co., Ltd.).

The resulting fused cells were then suspended in IMDM medium containing 10% FBS and a fused cell growth stimulating-agent (BM-Condimed H1, available from Boehringer Mannheim Biochemicals) and dispensed into a 96-well plate for culturing at 37° C. in a 5% $CO_2$ incubator. On the following day, the cells were placed in the HAT selection medium and then the 10% FBS/IMDM medium containing the growth-stimulating agent, and culturing was continued to sustain growth.

In order to examine the effect of the culture supernatant of these fused cells on leukemia cell lines, the medium for fused cells was replaced with IMDM medium containing 10% FBS, and culturing was continued to sustain growth.

(3) Screening

The following screening was performed using the culture supernatant of the aforementioned fused cells.

[1] Primary Screening

Cells of a mouse spleen stromal cell line (CF-1 cells), transfected with the human Integrin Associated Protein (IAP) gene (recombinant cells into which the same plasmid was subcloned as the plasmid used to prepare the human IAP-expressing L1210 cells used for antigen sensitization) were seeded in a 96-well plate at $1 \times 10^4$ cells per well and cultured overnight, and then fixed with 2% PLP (periodate-lysine-paraformaldehyde) to prepare an ELISA plate. After rinsing, the plate was subjected to blocking for 1 h at room temperature using a 1% BSA solution, and after further rinsing, 50 µl of the culture supernatant of each hybridoma was added for incubation at room temperature for one hour.

After rinsing, anti-mouse IgG+A+M (H+L) (Zymed Laboratories Inc.) labeled with alkaline phosphatase was added prior to incubation at room temperature for 1 h. After rinsing, SIGMA 104 substrate (Sigma-Aldrich, Corporation) was added to provide a final concentration of 1 mg/ml, incubation was continued at room temperature, and the specific activity was measured with a microplate reader (Model 3550, available from BioRad Laboratories Inc.).

As a result, appearance of hybridomas was confirmed in 2089 wells among the hybridomas seeded in 2880 wells, with 187 wells being positive in the primary screening. 50 µl each of Mouse IgG1 as a negative control and anti-human CD47 antibody (BD PharMingen) as appositive control were added at a concentration of 3 µg/ml, respectively, prior to incubation at room temperature for 1 h.

[2] Secondary Screening

The clones judged as positive in the primary screening were subjected to an ELISA system using human Integrin Associated Protein (IAP)-expressing CF-1 cells, where the negative control was CF-1 cells transfected with only the expression vector pCOS1, in order to screen whether the antibodies produced by the hybridomas would specifically recognize human IAP.

As a result, the positive was confirmed for 21 of the 187 wells found to be positive in the primary screening. Table 1 shows the specific binding of human IAP with 7D2 and 11C8 as representative examples among these, in terms of the absorbance in ELISA.

(Table 1) ELISA analysis of specific binding of hybridoma culture supernatants with human IAP

TABLE 1

|  | PBS | αhCD47 3 µg/ml | 7D2 | 11C8 |
|---|---|---|---|---|
| <Raw data> | | | | |
| CF1-pCOS1 | 0.185 | 0.160 | 0.189 | 0.149 |
| CF1-hIAP-55-8 | 0.192 | 0.456 | 0.568 | 0.812 |
| <Subtracted> | | | | |
| Specific binding | 0.007 | 0.296 | 0.379 | 0.663 |

[3] Tertiary Screening

The clones judged to be positive in the secondary screening were subjected to a growth inhibition, test using Jurkat cells (human T cell lymphoma line) and ARH77 cells (human myeloma cell line). 100 µl of the Jurkat cells at $5 \times 10^3$ cells per well and the ARH77 cells at $1 \times 10^4$ cells per well were seeded in each well of a 96-well plate, and 5 or 10 µl of culture supernatant of the hybridoma clones were added to the cell suspensions. After culturing for about 2 days, the cell numbers were measured by MTS assay. As a control, 5 or 10 µl each of IMDM medium containing 10% FBS and culture supernatants of clones that were negative in the primary screening (8G2 and 9C5) were added.

Figure 5:
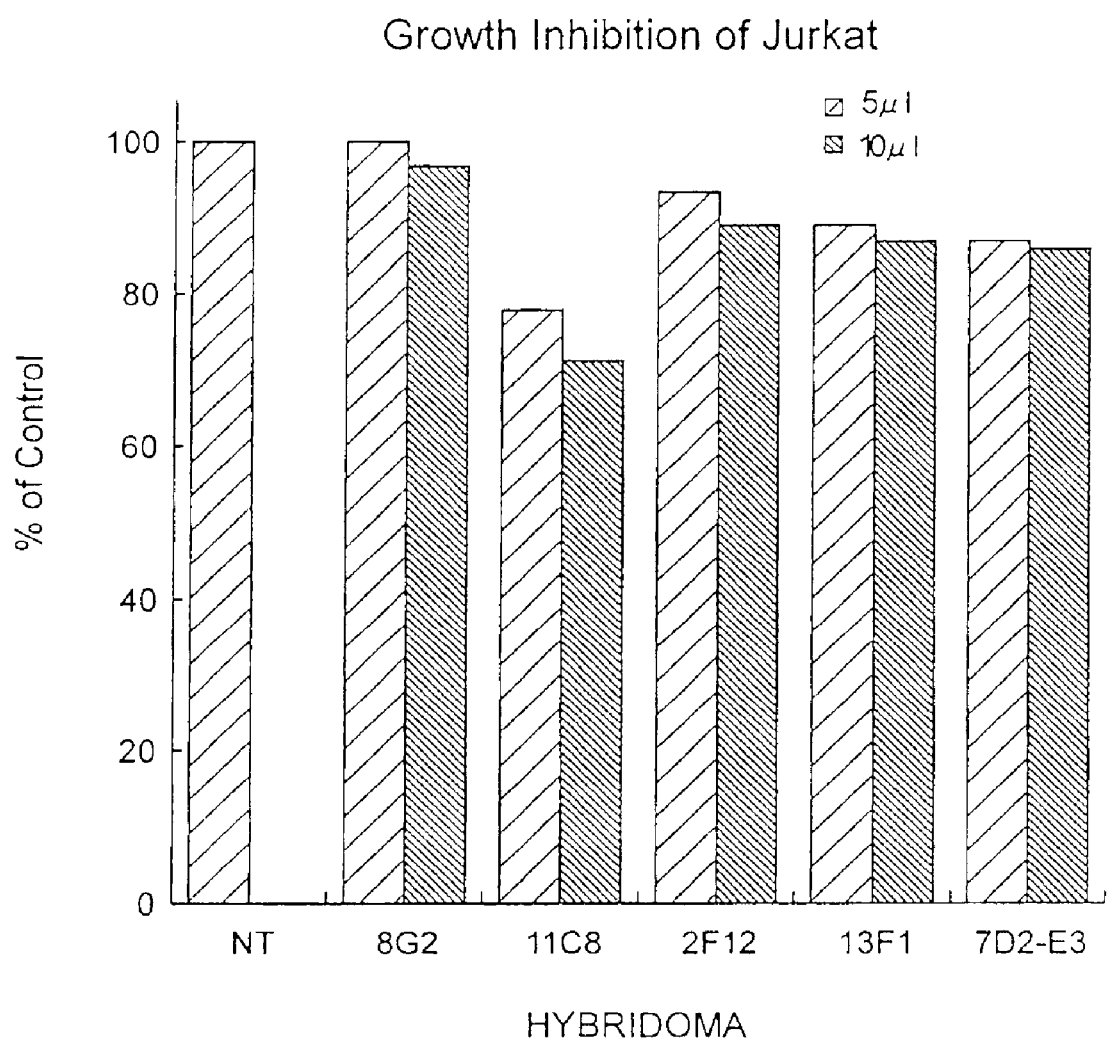
FIG. 5 is a bar graph showing the results of a growth inhibition experiment (Jurkat cells) using a hybridoma culture supernatant.
Figure 6:
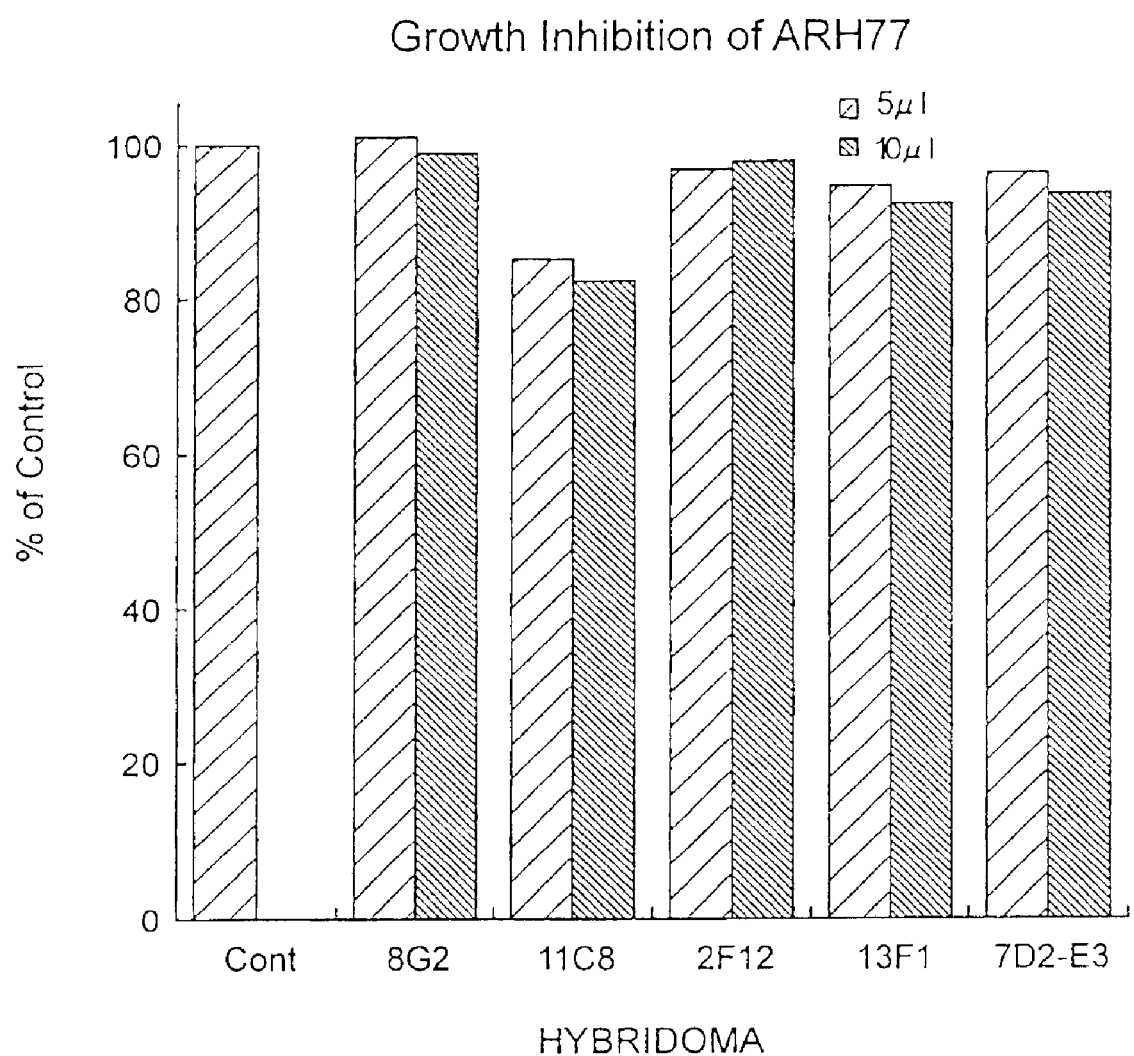
FIG. 6 is a bar graph showing the results of a growth inhibition experiment (ARH77 cells) using a hybridoma culture supernatant.
Figure 7:
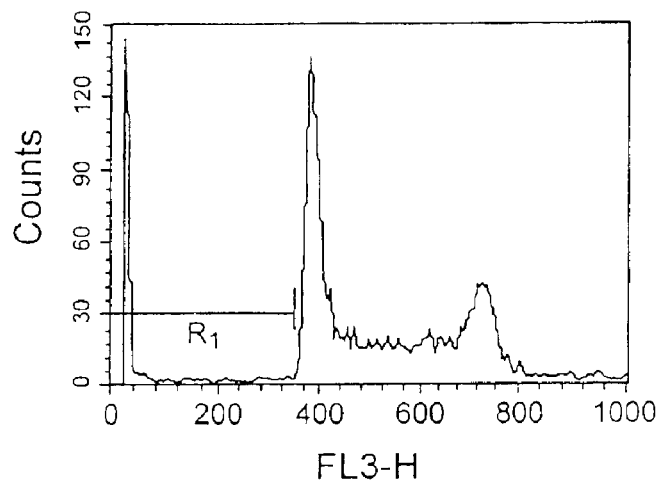
FIG. 7 is a graph showing the apoptosis-inducing effect on Jurkat cells by a culture supernatant (as analyzed by PI staining), which is the result for an 8G2 culture supernatant used as a control. R1 indicates the percentage (%) of apoptosis, which is 7.43%.
Figure 8:
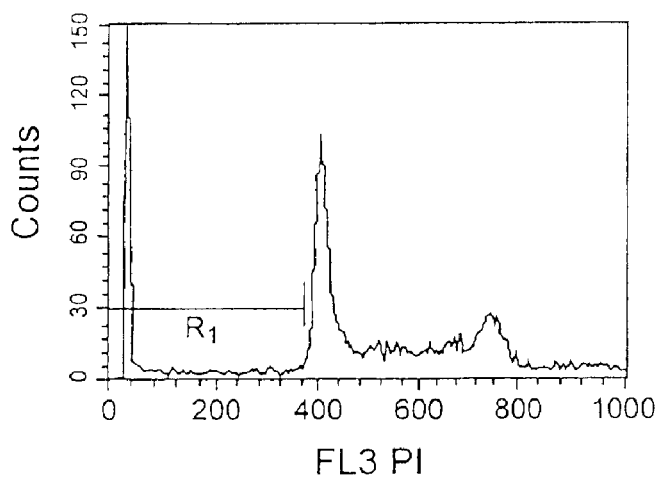
FIG. 8 is a graph showing the apoptosis-inducing effect on Jurkat cells by a culture supernatant (as analyzed by PI staining), which is the result for 7D2-E3. R1 indicates the percentage (%) of apoptosis, which is 9.84%.
Figure 9:
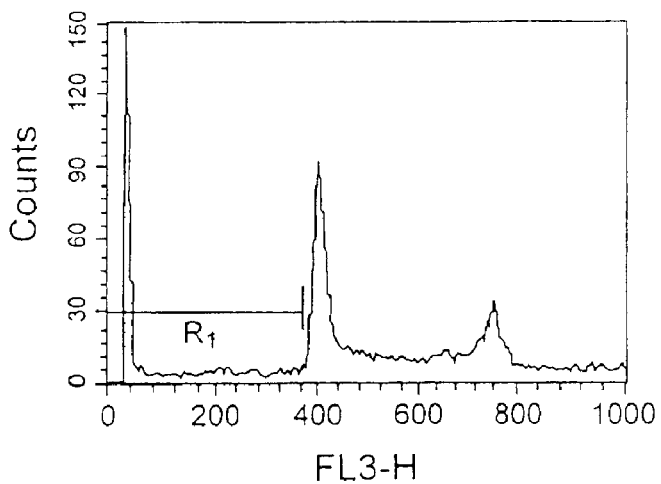
FIG. 9 is a graph showing the apoptosis-inducing effect on Jurkat cells by a culture supernatant (as analyzed by PI staining), which is the result for 11C8. R1 indicates the percentage (%) of apoptosis, which is 15.32%.
Figure 10:
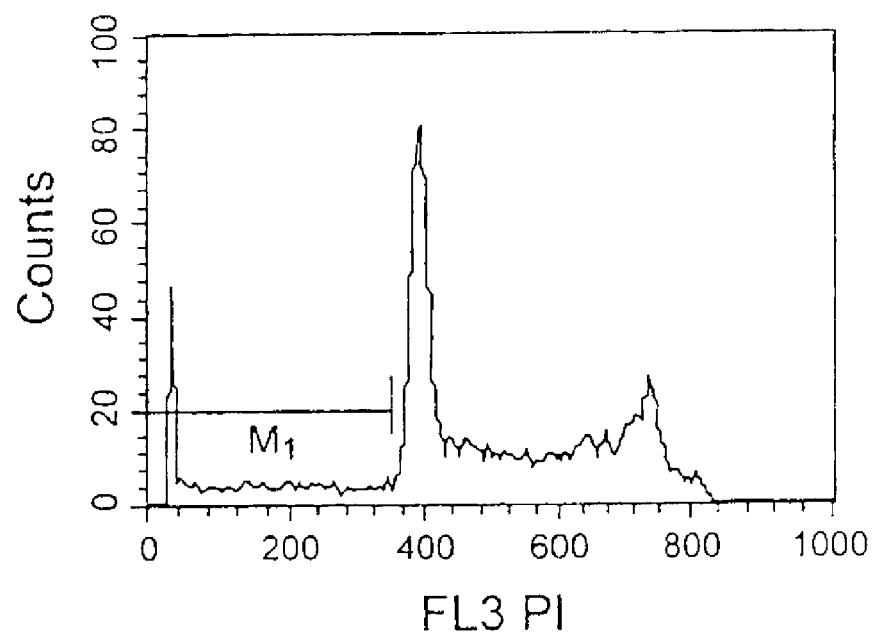
FIG. 10 is a graph showings the apoptosis-inducing effect on HL60 cells by a culture supernatant (as analyzed by PI staining), which is the result for an 8G2 culture supernatant used as a control. M1 indicates the percentage (%) of apoptosis, which is 6.94%.
Figure 11:
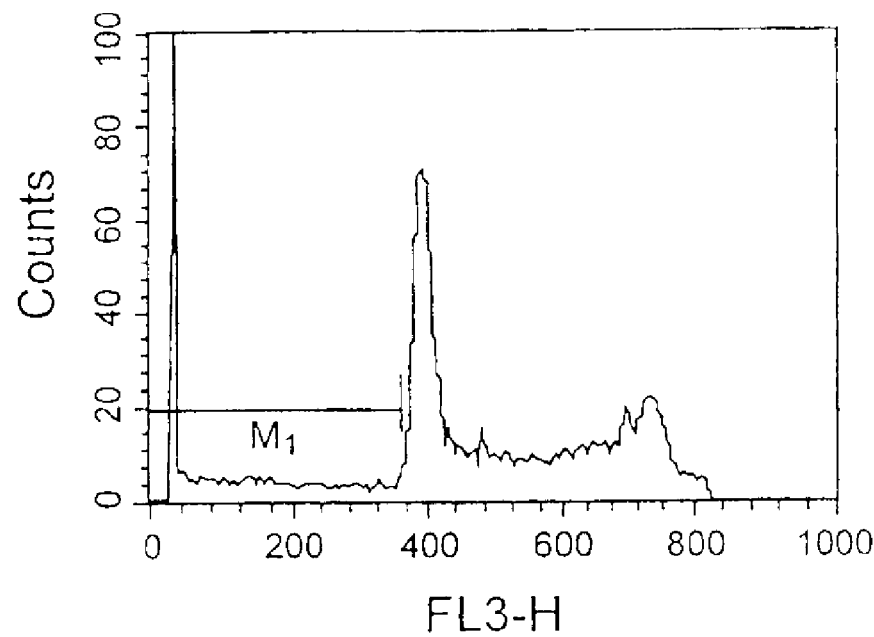
FIG. 11 is a graph showing the apoptosis-inducing effect on HL-60 cells by a culture supernatant (as analyzed by PI staining), which is the result for 11C8. M1 indicates the percentage (%) of apoptosis, which is 12.16%.

FIGS. 5 and 6 show the results of the growth inhibition effect of four representative clones, 11C8, 7D2-E3 (subclone of 7D2), 13F1 and 2F12.

(4) Antibody Properties

[1] The immunoglobulin types of the culture supernatants of 11C8, 7D2-E3, 13F1 and 2F12 were examined using an ELISA system.

Specifically, human Integrin Associated Protein (IAP)-expressing CF-1 cells were seeded into a 96-well plate to prepare an ELISA plate, and then 50 µl of each culture supernatant was added, alkaline phosphatase-labeled anti-mouse IgG antibody (Zymed Laboratories Inc.) or anti-mouse IgM antibody (Biosource Intl., Inc.) were reacted therewith as secondary antibodies, and the activity was measured with a microplate reader. As a result, 11C8 and 7D2-E3 were confirmed to be IgG, while 13F1 and 2F12 were confirmed to by IgM.

[2] The DNA fragmentation of the two clones 11C8 and 7D2-E3 among the four clones described above was analyzed by flow cytometry (FACScan, available from Becton, Dickinson and Company) using Jurkat cells and HL-60 cells. The Jurkat cells were used for 11C8 and 7D2-E3, and the HL-60 cells were used for 11C8.

The Jurkat-cells and HL-60 cells were seeded in a 12-well plate at $4 \times 10^4$ cells per well/2 ml, respectively, and 200 µl of the culture supernatants of 7D2-E3 and 11C8 were added. The cells were cultured for 2 days, and measured. As a control, 8G2 culture supernatant was added in an equal volume. The cells were recovered from the culturing plate and a cell pellet was fixed under 200×g, for 60 minutes at 4° C. in 2 ml of chilled 70% ethanol. The cells were then centrifuged, rinsed in 1 ml of PBS and resuspended in 0.5 ml of PBS. To a 0.5 ml sample of the cells, 0.5 ml of RNAse (Type I-A, Sigma-Aldrich Corporation, St. Louis, Mo., USA; 1 mg/ml in PBS) was added, and these were mixed with a 1 ml propidium iodide solution (PI, Sigma, 100 µg/ml in PBS). The mixed cells were incubated for 60 min in a darkroom at 37° C., and then kept in the darkroom at 4° C. and measured by flow cytometry.

As shown in FIGS. 7-9 and 10-11, the culture supernatants of 7D2-E3 and 11C8 increase a proportion of apoptosis cells of Jurkat cells and the culture supernatant of 11C8 increases a proportion of apoptosis cells of HL-60 cells, respectively.

[3] The culture supernatants of 11C8 were used in a coculturing system with HL-60 cells using a feeder layer of cells of the human myeloid stromal cell line KM102, to determine whether these culture supernatants induce apoptosis of HL-60 cells.

Figure 12A:
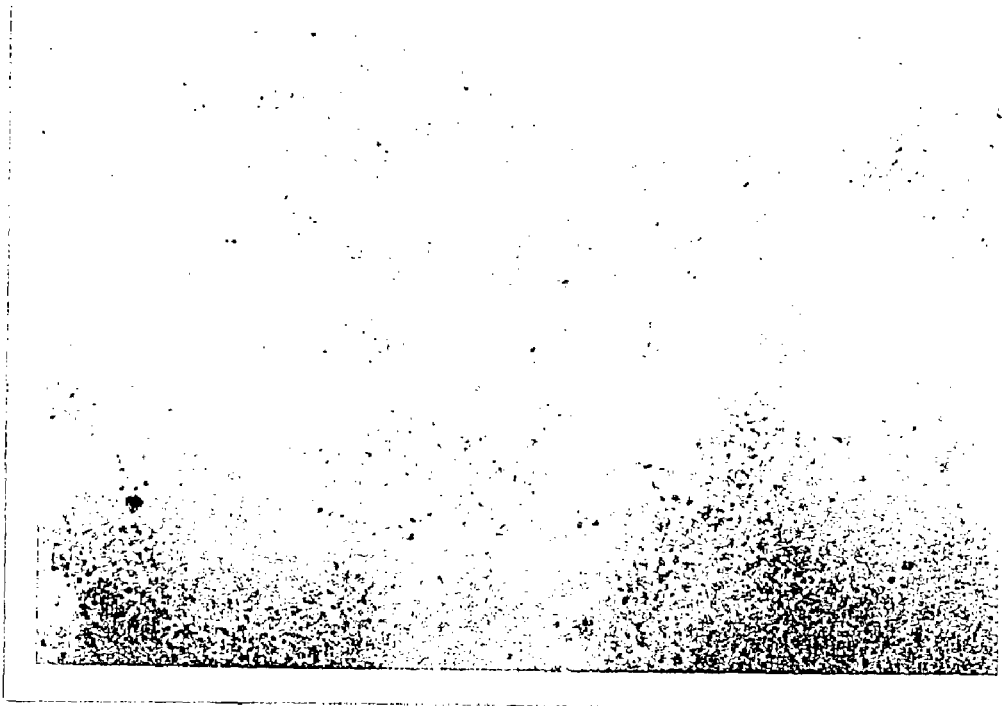
FIG. 12A is a monochrome photomicrograph showing the result of apoptosis analysis (TUNEL method) in a coculturing system with KM-102 and HL-60 cells, using 9C5 culture supernatant as a control. The apoptotic cells are stained black or brown. The nuclear staining wasp accomplished with Methyl Green, and the magnification is 100×.
Figure 12B:
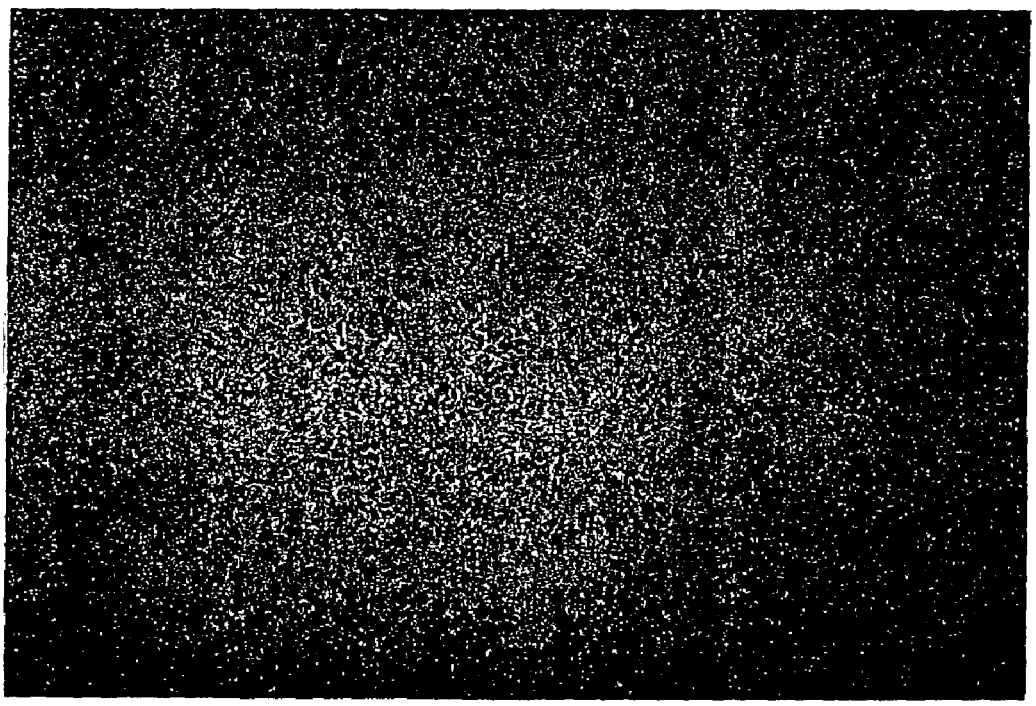
FIG. 12B is a color photomicrograph showing the result of apoptosis analysis (TUNEL method) in a coculturing system with KM-102 and HL-60 cells, using 9C5 culture supernatant as a control. The apoptotic cells are stained black or brown. The nuclear staining was accomplished with Methyl Green, and the magnification is 100×.
Figure 13A:
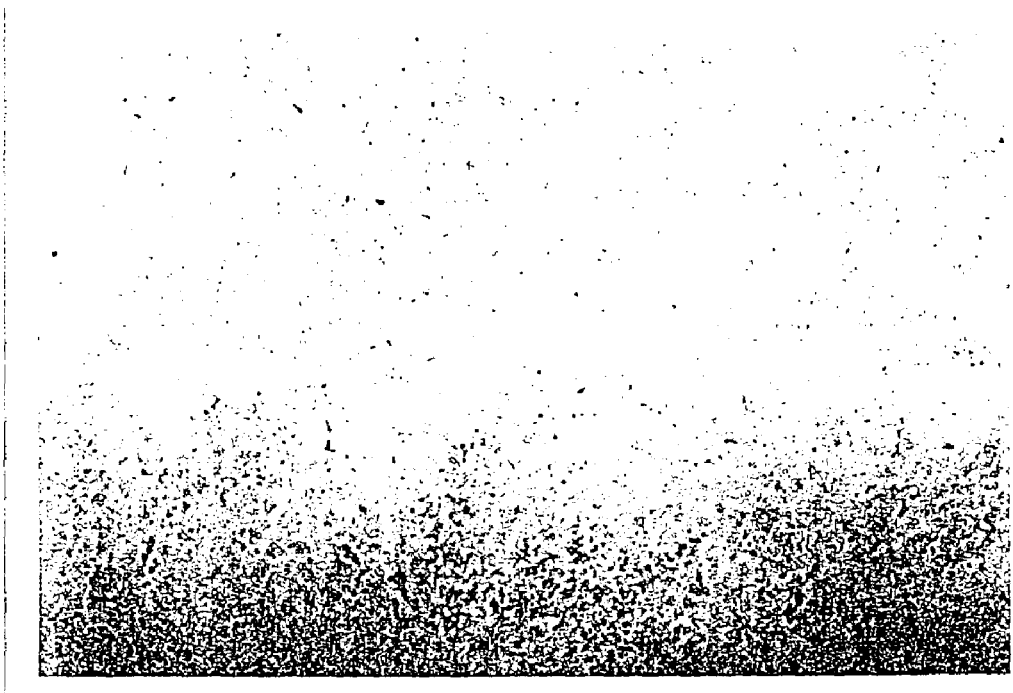
FIG. 13A is a monochrome photomicrograph showing the result of apoptosis analysis (TUNEL method) in a coculturing system with KM-102 and HL-60 cells, using 11C8 culture supernatant. More TUNEL-positive cells are seen than in FIG. 12. The apoptotic cells are stained black or brown. The nuclear staining was accomplished with Methyl Green, and the magnification is 100×.
Figure 13B:
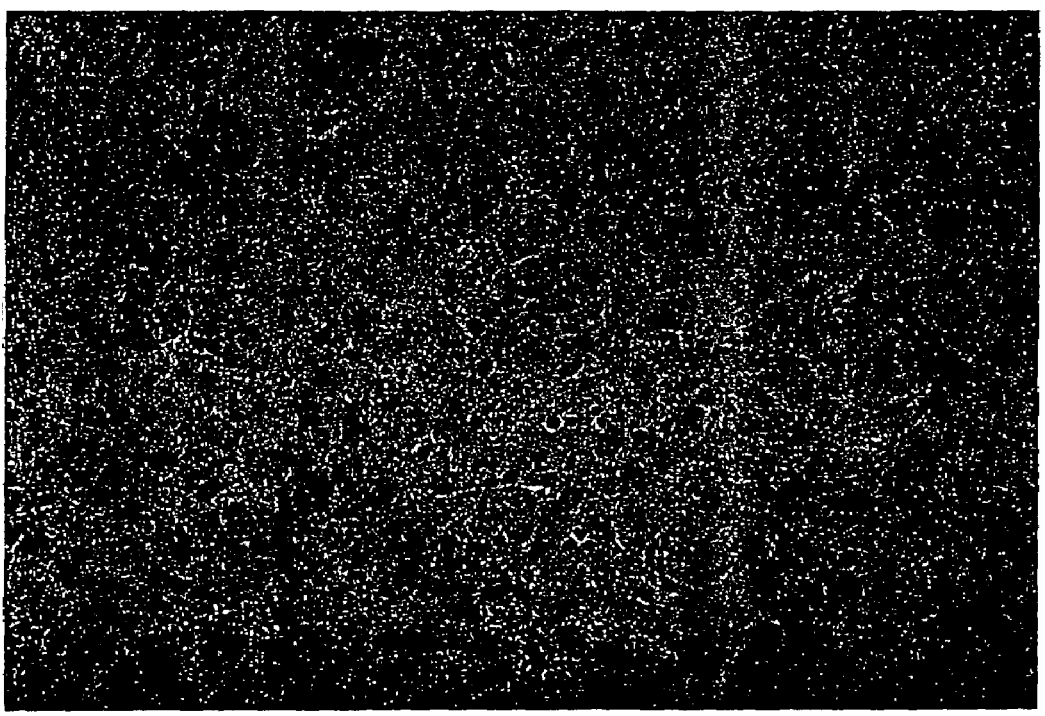
FIG. 13B is a color photomicrograph showing the result of apoptosis analysis (TUNEL method) in a coculturing system with KM-102 and HL-60 cells, using 11C8 culture supernatant. More TUNEL-positive cells are seen than in FIG. 12. The apoptotic cells are stained black or brown. The nuclear staining was accomplished with Methyl Green, and the magnification is 100×.

Specifically, KM102 cells were seeded in a 2-well Lab-Tek Chamber Slide (Nalge Nunc Intl. Corporation) and brought to a sub-confluent state, $1\times10^5$ cells of HL-60 cells were seeded thereon and cultured for about one day, and then the non-attached HL-60 cells were removed. The aforementioned culture supernatants were simultaneously added to provide a final concentration of 10% and the cells were cultured for 2 days. After culturing, the cells were fixed with 10% formalin and the apoptosis-induced HL-60 cells were detected by the TUNEL method (ApopTag Plus available from Oncor Inc.). As shown in FIGS. 12 and 13, the culture supernatant of 11C8 more increases apoptosis cells of HL-60 cells than the culture supernatant of 9C5 does, which is the culture supernatant of the human IAP non-reacting hybridoma clone used as the control.

(5) Antibody Purification

Figure 14:
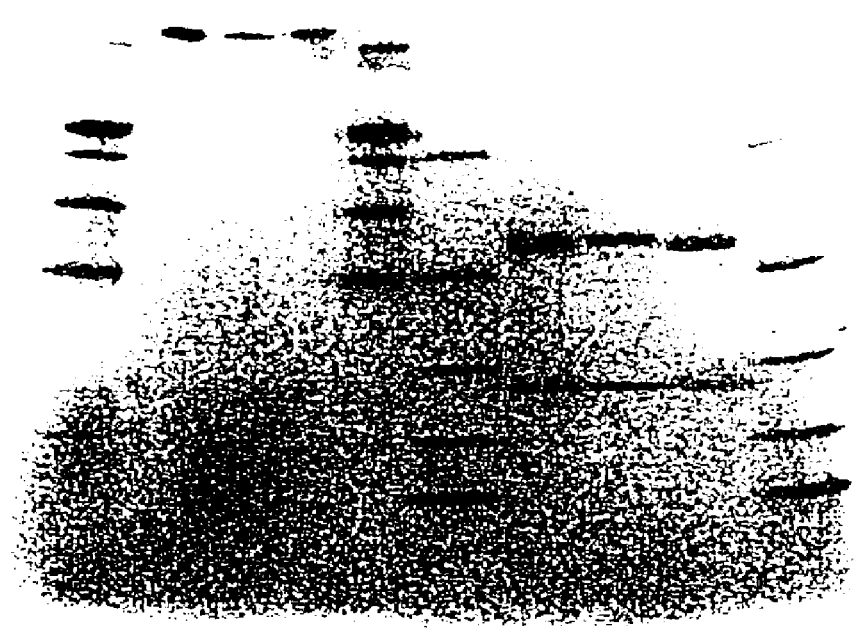
FIG. 14 is an electrophoresis pattern showing the results of SDS-PAGE analysis of IgG purified from hybridoma lines 7D2-E3 and 11C8. Shown are molecular weight markers (M, M'), mouse IgG (authentic sample) under non-reducing conditions (1), 7D2-E3 (2), 11C8 (3), mouse IgG (authentic sample) under reducing conditions (4), 7D2-E3 (5) and 11C8 (6).

For purification of the antibodies produced by hybridomas, the cell lines of the IgG-producing clones 7D2-E3 and 11C8 among the above hybridoma lines were intraperitoneally injected into pristane-administered BALB/c/AnNCrj mice (male, available from Charles River, Japan) according to a standard method. After several weeks, the ascites fluid produced was taken and the antibodies were separated and purified by standard methods. Specifically, the antibodies were purified from the obtained ascites fluid by a Polos Protein A plastic column (Perceptive Biosystems Inc.) and dialyzed with PBS (Dulbecco Inc.), and bands were confirmed with SDS-PAGE analysis. As shown in FIG. 14, electrophoresis using an authentic sample of mouse IgG (Cappel Inc.) as a control confirmed bands for the IgG of clones 7D2-E3 and 11C8 at the same positions as the authentic sample mouse IgG, under both non-reducing conditions and reducing conditions.

In this example, the human Integrin Associated Protein (IAP)-expressing L1210 cells were used as the sensitizing antigen for illustrative purposes, but it is also possible to prepare monoclonal antibodies in the same manner using other human IAP-expressing cells or human IAP itself, and to prepare monoclonal antibodies from an antibody library using the phage display method; this invention is not limited to the aforementioned monoclonal antibodies but encompasses all monoclonal antibodies with properties similar thereto and all hybridomas that produce those monoclonal antibodies.

Furthermore, the invention of these monoclonal antibodies also includes humanized antibodies, human antibodies, chimeric antibodies, single-chain antibodies, primatized antibodies and antibody fragments obtained by digesting the antibodies with various enzymes (papain, pepsin, ficin, etc.).

The hybridomas producing the monoclonal anti-human Integrin Associated Protein (IAP) antibodies of the invention are novel fused cells created from DBA mice spleen cells and the mouse myeloma cell line P3-U1 as the parent cells; anti-IAP antibody (mouse hybridoma 11C8-F8 (subclone of 11C8), designated as "MABL-2") was deposited as FERM BP-6100 and anti-IAP antibody (mouse hybridoma 7D2-E3 (subclone of 7D2), designated as "MABL-2") as FERM BP-6101 on Sep. 1, 1997 with the National Institute of Bioscience and Human Technology, Agency of Industrial Science and Technology, Ministry of International Trade and Industry, located at 1-3 Higashi 1-chome, Tsukuba-shi, Ibaraki-ken, Japan, as an authorized depository for public microorganisms.

Example 2

Subclass Identification of MABL-1 and MABL-2 Antibodies

In order to identify the subclasses of MABL-1 and MABL-2 antibodies obtained above, 500 μl each of MABL-1 and MABL-2 adjusted to 100 ng/ml was spotted on an Isotyping Kit (Stratagene), by which MABL-1 was shown to be IgG1, κ and MABL-2 was shown to be IgG2a, κ.

Example 3

Human IAP-Expressing Human Leukemia Cells

Figure 15:
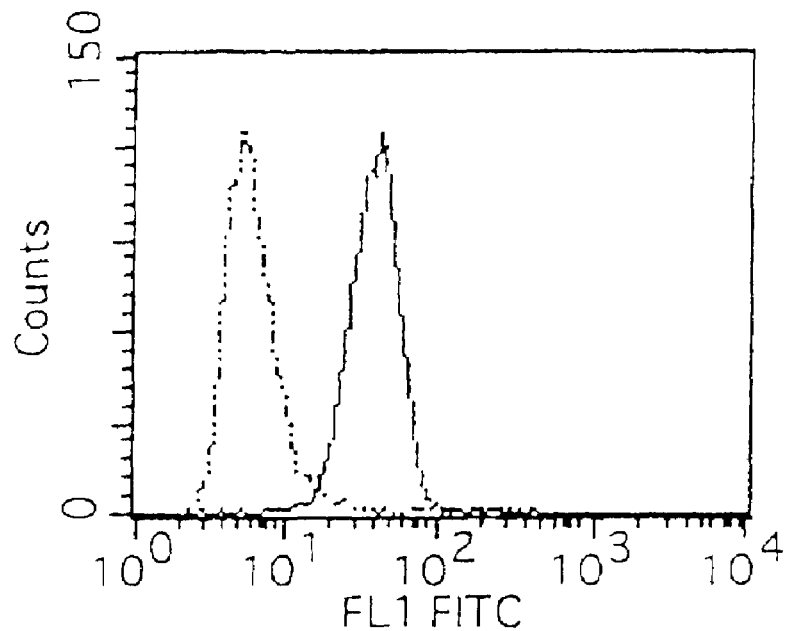
FIG. 15 shows the results of analysis of CD47 expression by flow cytometry, using HL-60 cells.
Figure 16:
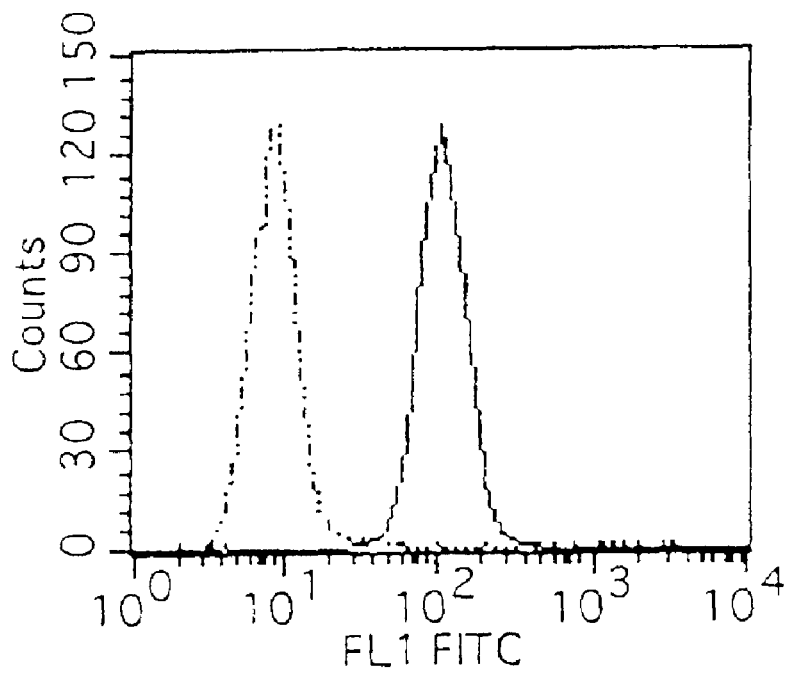
FIG. 16 shows the results of analysis of CD47 expression by flow cytometry, using Jurkat cells.
Figure 17:
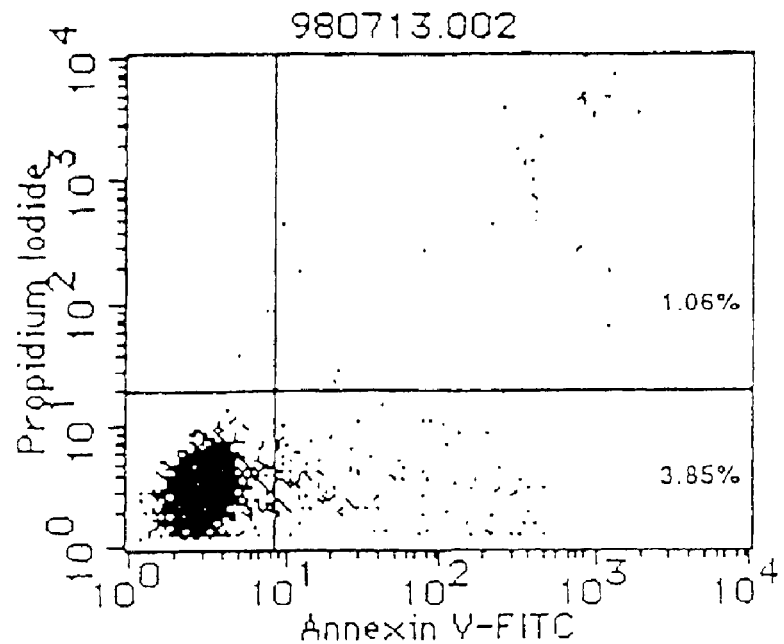
FIG. 17 shows results for mIgG (10 μg/ml) as a control to demonstrate its apoptosis-inducing effect on L1210 cells transfected with the human IAP gene (L1210-hIAP). (incubation for 72 hours).
Figure 18:
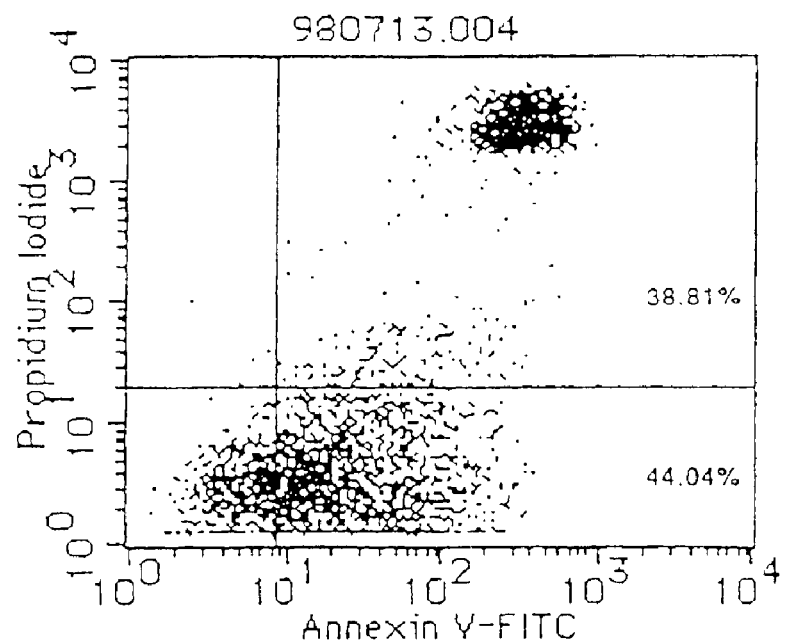
FIG. 18 shows the apoptosis-inducing effect of MABL-1 (10 μg/ml) on L1210 cells transfected with the human IAP gene (incubation for 72 hours).
Figure 19:
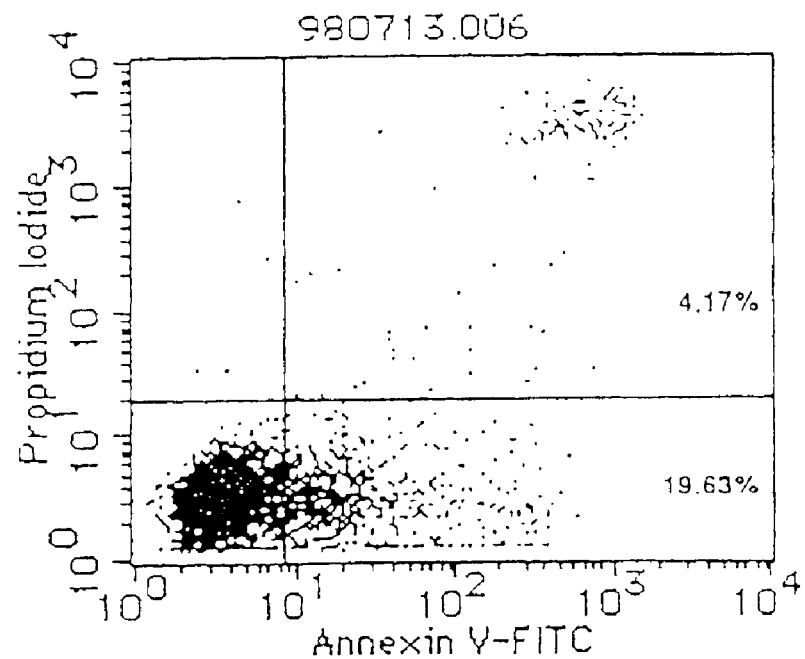
FIG. 19 shows the apoptosis-inducing effect of MABL-2 (10 μg/ml) on L1210 cells transfected with the human. IAP gene (incubation for 72 hours).
Figure 20:
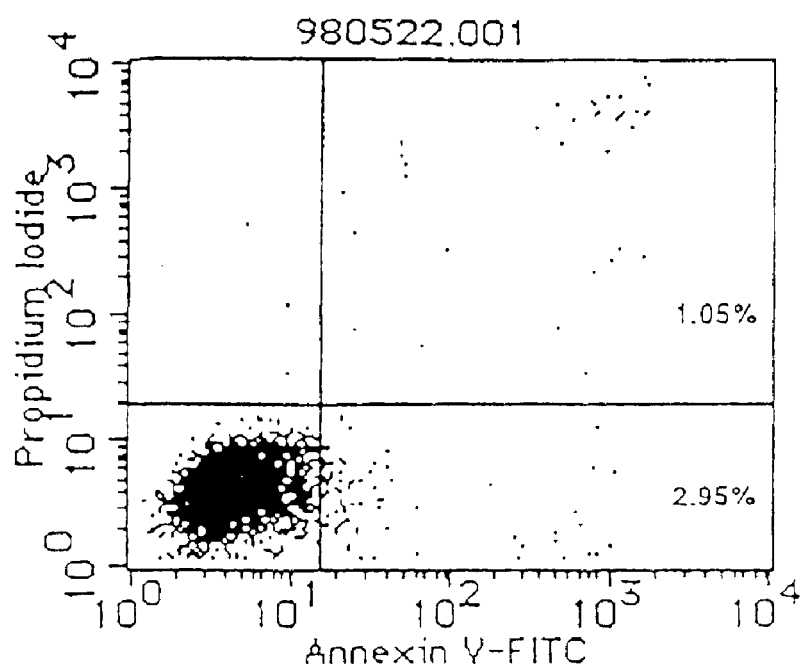
FIG. 20 shows results for mIgG (10 μg/ml) as a control to demonstrate its apoptosis-inducing effect on Jurkat cells (incubation for 48 hours).
Figure 21:
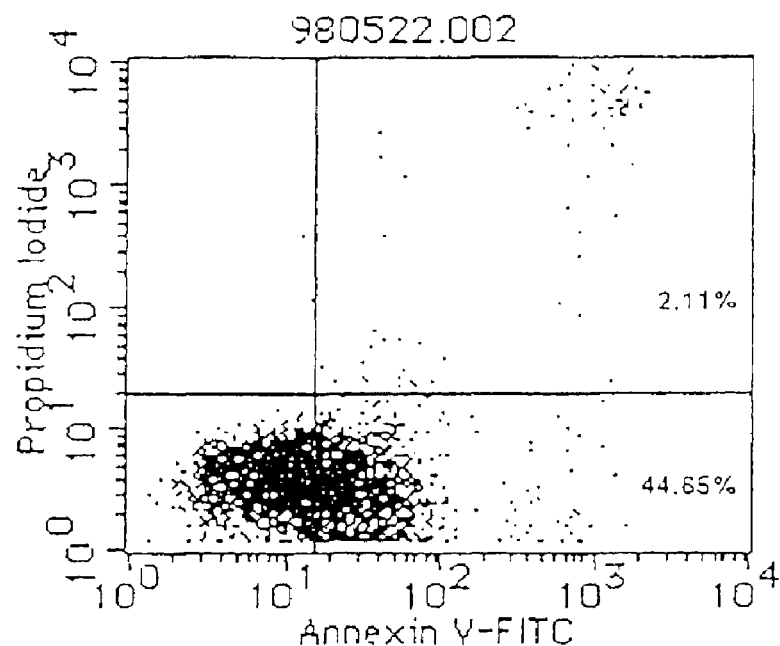
FIG. 21 shows the apoptosis-inducing effect of MABL-1 (10 μg/ml) on Jurkat cells (incubation for 48 hours).
Figure 22:
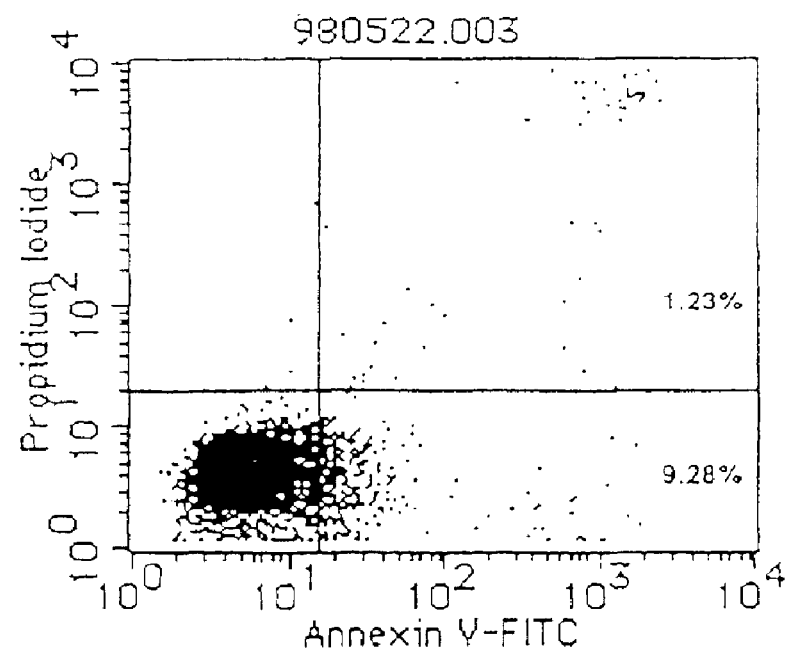
FIG. 22 shows the apoptosis-inducing effect of MABL-2 (10 μg/ml) on Jurkat cells (incubation for 48 hours).

IAP expression in different human leukemia cell lines was detected by flow cytometry with human IAP-recognizing anti-CD47 antibody (a commercially available product). This antibody was used for the detection because human IAP is believed to be identical to CD47 (Biochem. J., 304, 525-530, 1994). The cell lines used were Jurkat and HL-60 cells (K562 cells, ARH77 cells, Raji cells and CMK cells). The cells were used at $2\times10^5$ cells per sample, the anti-CD47 antibody was incubated with the cells at a final concentration of 5 μg/ml, and the secondary antibody used was FITC-labeled anti-mouse IgG antibody (Becton Dickinson and Company). Mouse IgG1 antibody (Zymed Laboratories Inc.) was used as a control. The results of the flow cytometry as shown in FIG. 15 (HL-60) and FIG. 16 (Jurkat) confirmed that both cell lines expressed IAP.

Example 4

Apoptotic Effect In Vitro (1) The apoptosis-inducing activity of the MABL-1 and MABL-2 antibodies on L1210 cells transfected with human IAP gene, Jurkat cells and HL-60 cells were examined using Annexin-V (Boehringer Mannheim). The results of analysis with Annexin-V are shown in FIGS. 17-22, wherein the dots in the lower left region indicate the live cells, those in the lower right region indicate apoptotic cells, and those in the upper right region indicate necrotic cells. The antibodies used were mouse IgG (Zymed Laboratories Inc.) as a control and MABL-1 and MABL-2 at 10 μg/ml, and after $4\times10^3$ cells of L1210 cells transfected with the human IAP gene were incubated for 72 h and $6\times10^4$ cells of the Jurkat cells were incubated for 48 h, they were analyzed with Annexin-V. Cell death was observed, as shown in FIGS. 17-22. For the HL-60 cells, 10 μg/ml of MABL-1 was used, and analysis with Annexin-V at $1\times10^5$ cells likewise revealed cell death.

Figure 23:
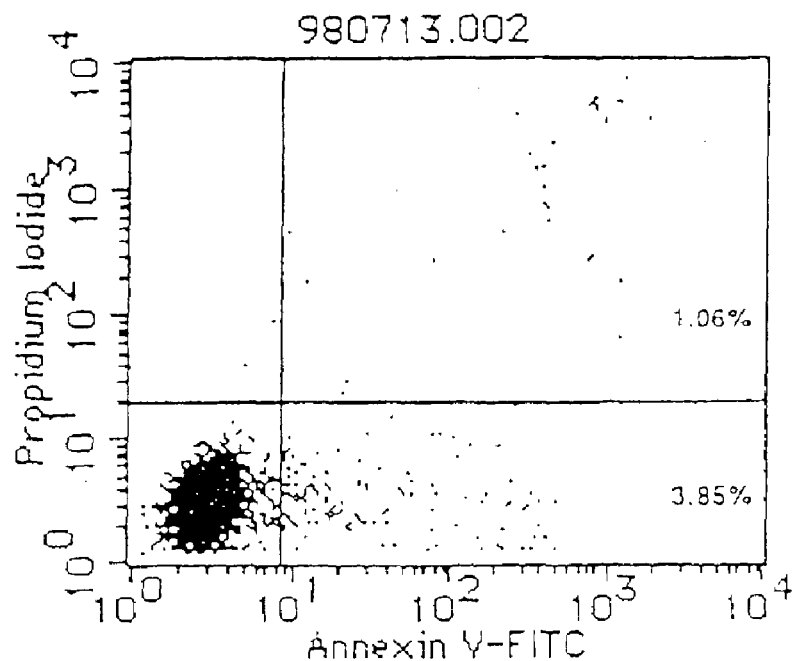
FIG. 23 shows results for mIgG (10 μg/ml) as a control to demonstrate its apoptosis-inducing effect on L1210 cells transfected with the human IAP gene introduced therein (L1210-hIAP) (incubations for 72 hours).
Figure 24:
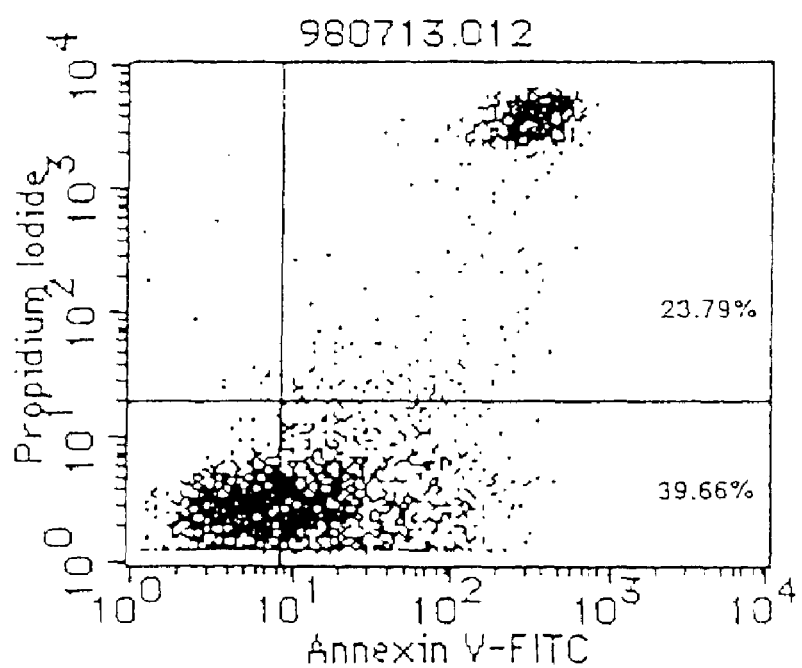
FIG. 24 shows the apoptosis-inducing effect of MABL-2 Fab fragments (10 μg/ml) on L1210 cells transfected with the human IAP gene.
Figure 25:
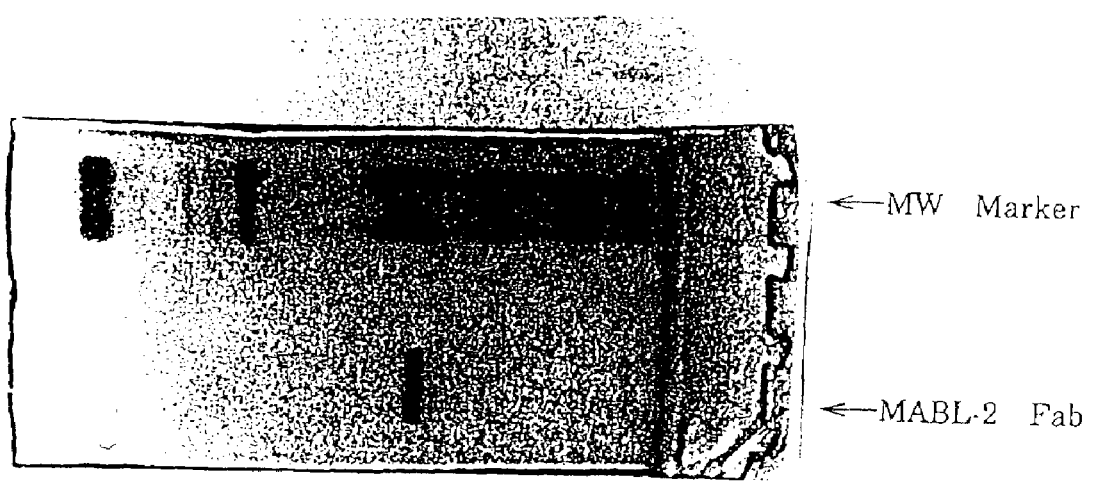
FIG. 25 is an SDS electrophoresis pattern for. MABL-2 antibody Fab fragments.

(2) The apoptosis-inducing activity of MABL-2 antibody Fab fragments on L1210 cells transfected with human IAP gene was examined. Specifically, L1210 cells transfected with human IAP gene were cultured at $4\times10^3$ cells, and MABL-2 antibody Fab fragments and mouse IgG as a control were used at a concentration of 10 μg/ml. The cells were incubated for 72 h and measured with Annexin-V. As a result, considerable cell death was observed (FIGS. 23, 24). The MABL-2 antibody Fab fragments used for the experiment were obtained by digesting the antibody with papain (Pierce Laboratories, Inc.) and purifying it. The MABL-2 antibody Fab fragments were analyzed by SDS electrophoresis (FIG. 25).

Example 5

Investigation of Apoptosis In Vivo (1) Drug Efficacy of MABL-1 and MABL-2 (Whole IgG)

Figure 26:
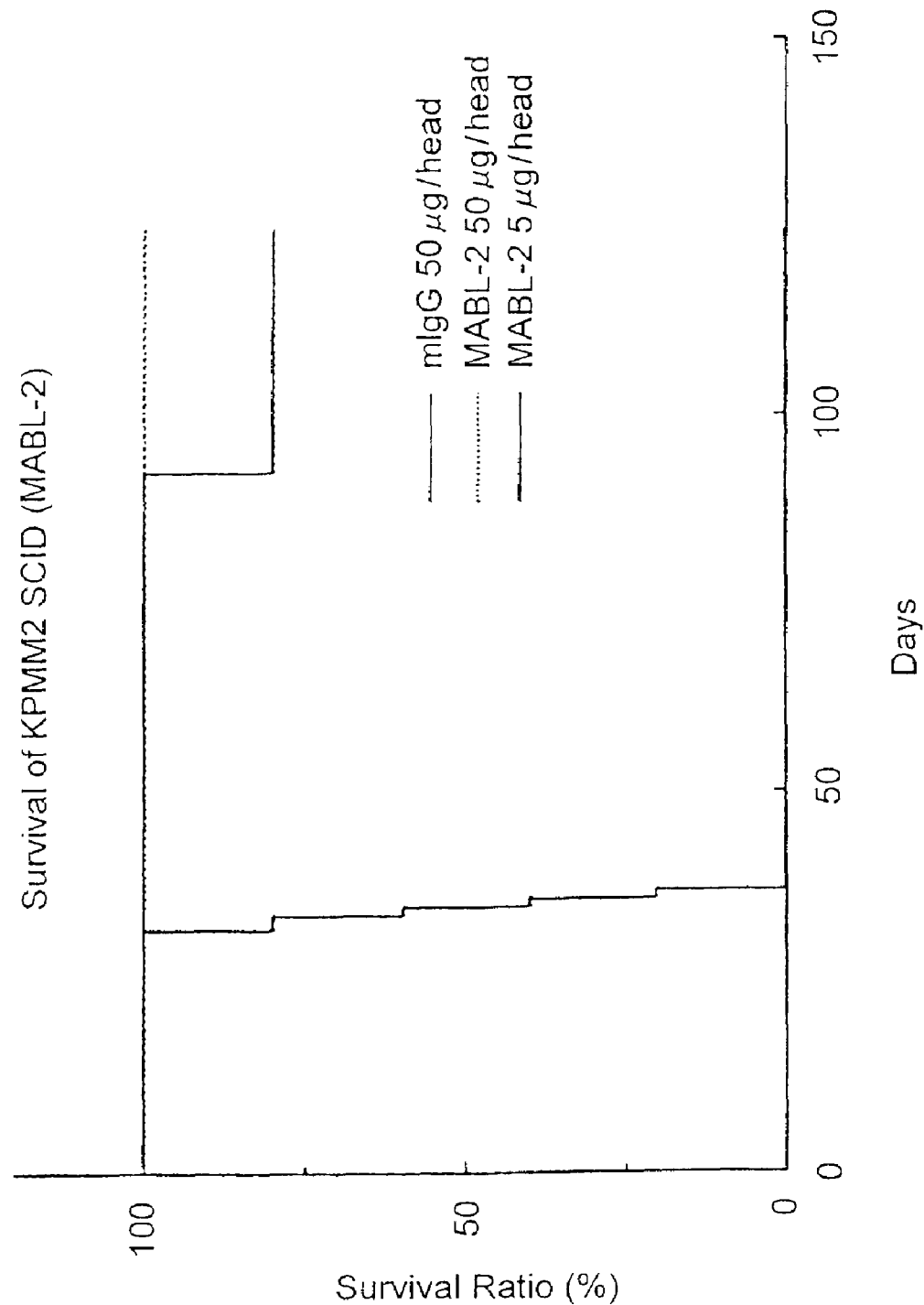
FIG. 26 shows a notably extended survival period upon treatment with MABL-2.
Figure 30:
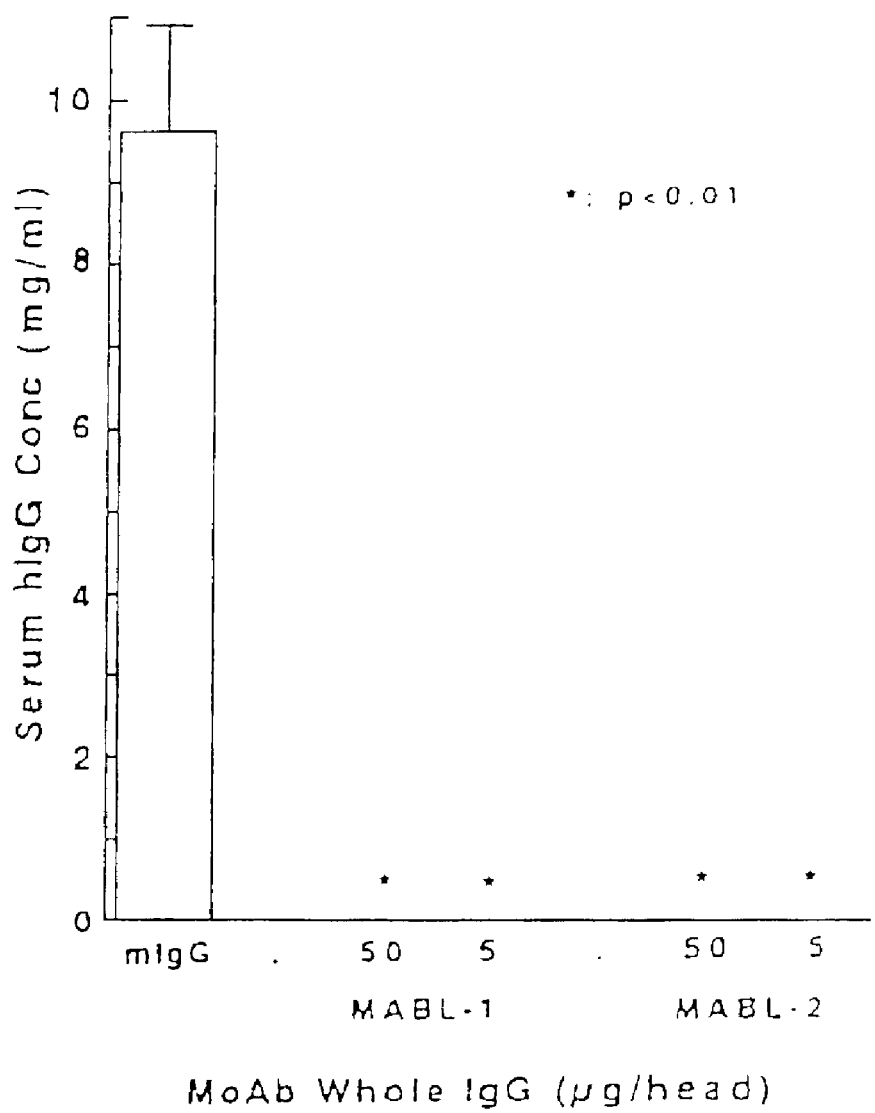
FIG. 30 shows that human IgG levels of mouse serum were decreased significantly in the groups treated with MABL-1 and MABL-2, which indicates anti-tumor effects of these antibodies.

Human IAP-expressing KPMM2 cells (human myeloma cell line) were transplanted into SCID mice, and on the 10th day after transplantation, MABL-1 and MABL-2 (whole IgG) were administered by single intravenous injection in a dose each of 5 µg/head and 50 µg/head, respectively (n=5); on the 28th day after KPMM2 transplantation, the human IgG levels derived from KPMM2 were measured by ELISA, and the disappearance was confirmed. The survival period was also examined. The results showed marked suppression of blood levels of human IgG in the groups treated with MABL-1 and MABL-2, which represented the anti-tumor effect (FIG. 30). The survival period was also shown to be notably lengthened (FIG. 26).

(2) Drug Efficacy of MABL-1 and MABL-2 (F(ab')$_2$)

Figure 27:
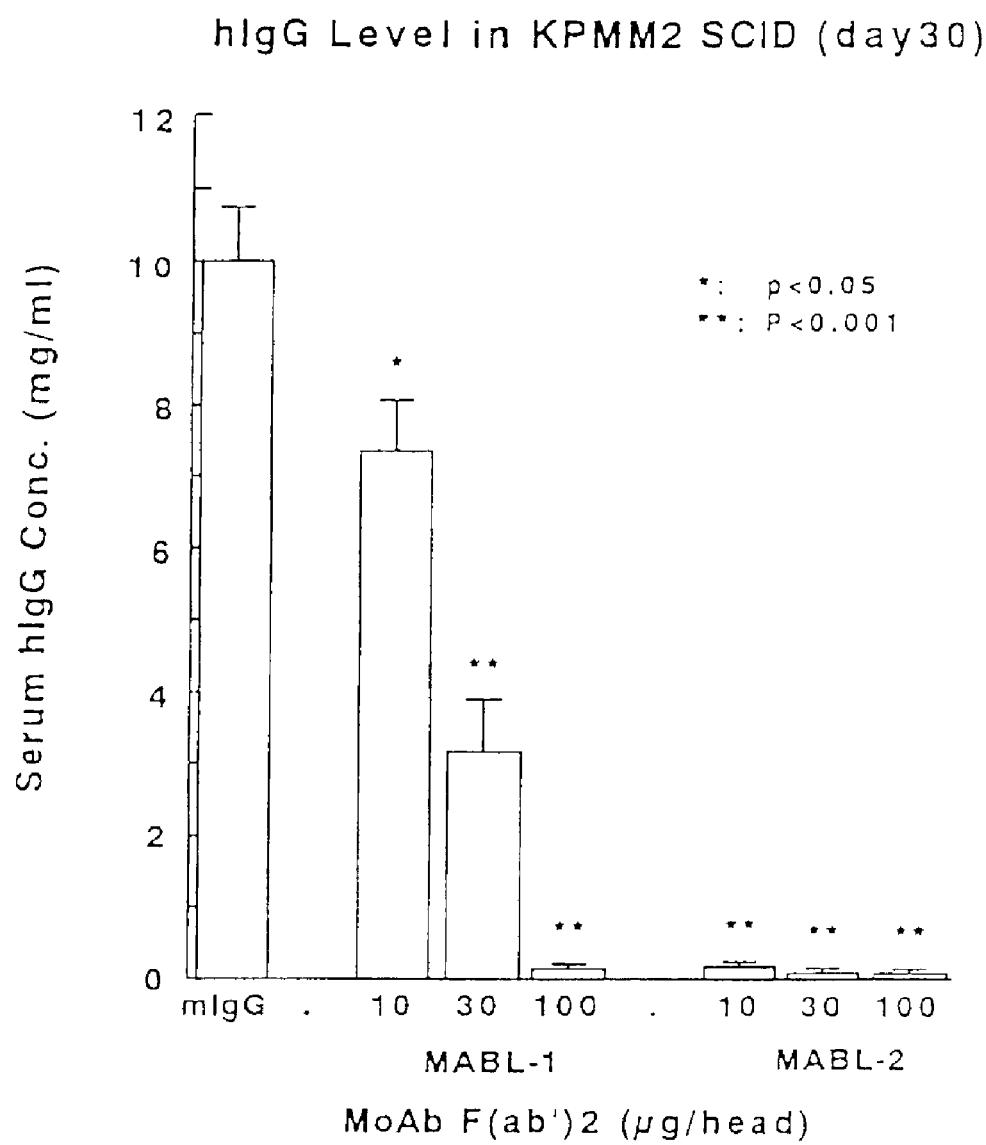
FIG. 27 shows the results of ELISA for Example 5(2).
Figure 28:
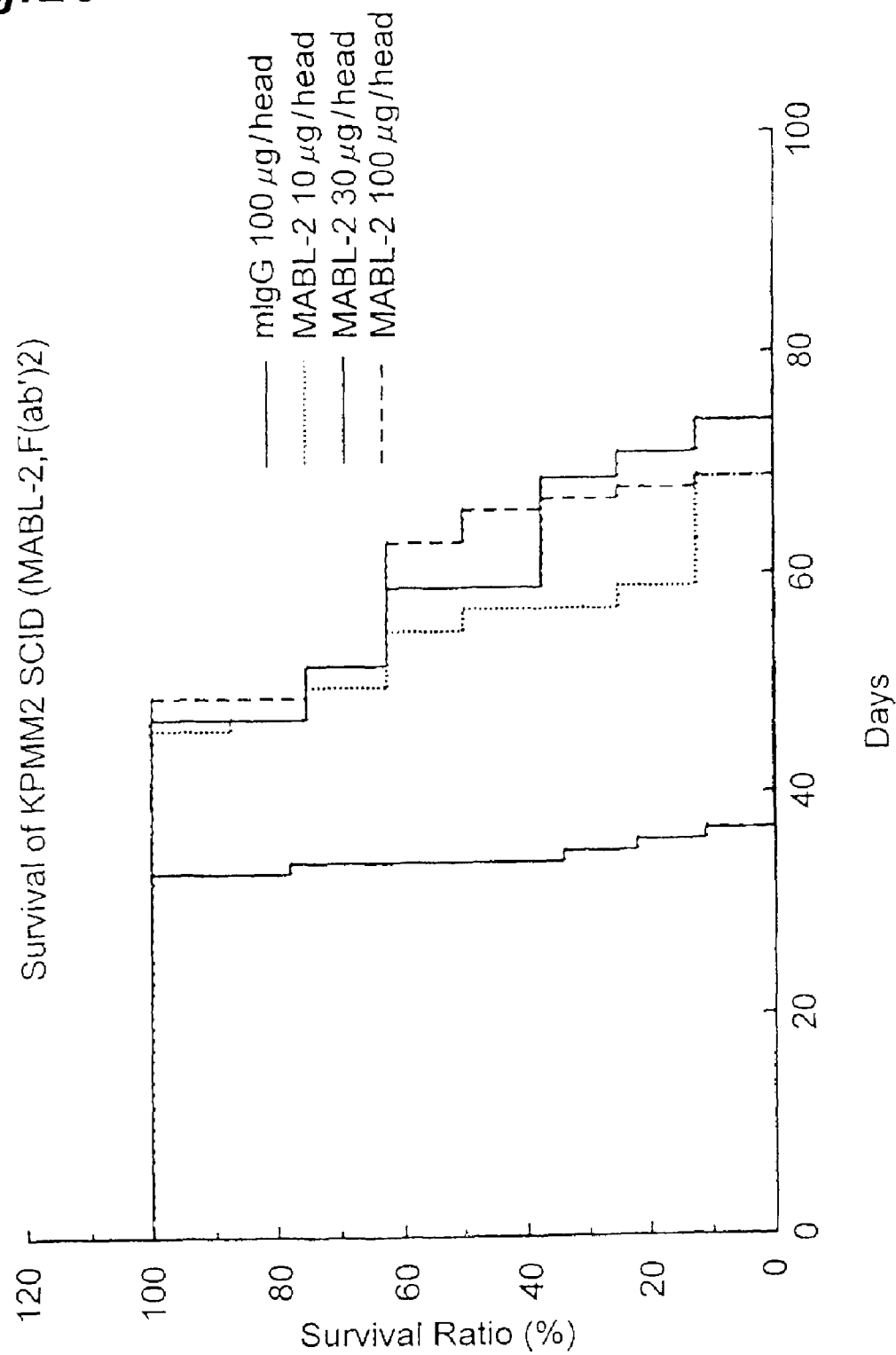
FIG. 28 shows a notably extended survival period upon treatment with MABL-2 F(ab')2 fragments.
Figure 29:
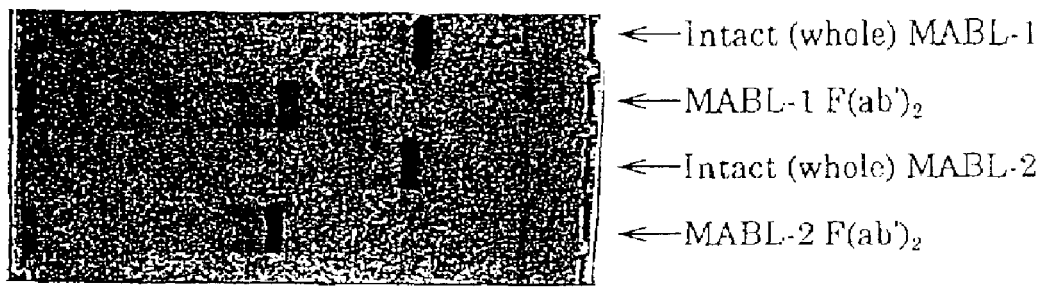
FIG. 29 is an SDS electrophoresis pattern for MABL-1 antibody and MABL-2 antibody F(ab')2 fragments.

F(ab')$_2$ fragments prepared by digestion of the MABL-1 and MABL-2 antibodies with pepsin and purification with Protein A (Pierce laboratories, Inc.) were used to examine the anti-tumor effect except the cytotoxic effect via the Fc regions. Specifically, human IAP-expressing KPMM2 cells (human myeloma cell line) were transplanted into SCID mice, and MABL-1 and MABL-2 F(ab')$_2$ fragments were intravenously administered to the groups in a dose of 100 µg/head on the 6th and 10th days after transplanting, and to the groups in a dose each of 10 and 30 µg/head on the 6th, 8th and 10th days after transplantation, respectively; the human IgG levels derived from KPMM2 were measured by ELISA on the 30th day after transplantation (FIG. 27). The survival period was also examined up to 90 days after transplanting. As a result, a notable suppressing effect on human IgG levels in the blood was found in the groups treated with MABL-1 and MABL-2, which represented the anti-tumor effect. The survival period was also considerably lengthened (FIG. 28). FIG. 29 shows the SDS electrophoresis pattern for the F(ab')$_2$ fragments of MABL-1 antibody and MABL-2 antibody.

INDUSTRIAL APPLICABILITY

The monoclonal antibodies of this invention are antibodies that specifically recognize human Integrin Associated Protein, and the antigens that induce apoptosis of nucleated blood cells having human Integrin Associated Protein. Accordingly, they are useful as antibodies that recognize human Integrin Associated Protein for its distinction and identification, while also having an action of inducing apoptosis of nucleated blood cells; these properties can be utilized to prepare useful therapeutic agents in the field of treatment for myeloid leukemia and lymphoid leukemia.

The invention claimed is:

1. A monoclonal antibody that recognizes and binds to a human Integrin Associated Protein (hIAP), wherein said monoclonal antibody is capable of inducing apoptosis of nucleated blood cells through binding to hIAP and is produced by hybridoma MABL-2 (deposit accession number FERM BP-6101) or hybridoma MABL-1 (deposit. accession number FERM BP-6100).

2. A fragment of a monoclonal antibody that is capable of inducing apoptosis of nucleated blood cells expressing hIAP through binding to hIAP, wherein the monoclonal antibody is defined in claim 1.

3. A hybridoma that produces a monoclonal antibody as defined in claim 1.

* * * * *

UNITED STATES PATENT AND TRADEMARK OFFICE
CERTIFICATE OF CORRECTION

PATENT NO. : 7,531,643 B2  Page 1 of 1
APPLICATION NO. : 10/355236
DATED : May 12, 2009
INVENTOR(S) : Fukushima et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 249 days.

Delete the phrase "by 249 days" and insert -- by 437 days --

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,531,643 B2 | Page 1 of 1 |
| APPLICATION NO. | : 10/355236 | |
| DATED | : May 12, 2009 | |
| INVENTOR(S) | : Fukushima et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this
Twentieth Day of September, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 1
gcaagcttat gtggcccctg gtagcg                                        26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 2
gcggccgctc agttattcct aggagg                                        26